(12) United States Patent
Blattner et al.

(10) Patent No.: US 6,855,814 B2
(45) Date of Patent: Feb. 15, 2005

(54) SEQUENCES OF E. COLI O157

(75) Inventors: Frederick R. Blattner, Madison, WI (US); Valerie Burland, Cross Plains, WI (US); Nicole T. Perna, Madison, WI (US); Guy Plunkett, Madison, WI (US); Rod Welch, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/114,170

(22) Filed: Apr. 1, 2002

(65) Prior Publication Data

US 2003/0023075 A1 Jan. 30, 2003

Related U.S. Application Data

(63) Continuation of application No. 09/453,702, filed on Dec. 3, 1999, now Pat. No. 6,365,723.
(60) Provisional application No. 60/110,955, filed on Dec. 4, 1998.

(51) Int. Cl.[7] ............................ C12Q 1/68; C07H 21/02
(52) U.S. Cl. ........................ 536/23.1; 536/24.3; 435/6
(58) Field of Search ............................... 536/23.1, 24.3; 435/6

(56) References Cited

U.S. PATENT DOCUMENTS

6,365,723 B1 * 4/2002 Blattner et al. ............ 536/23.1

OTHER PUBLICATIONS

Burland et al. "The complete DNA sequence and analysis of the large virulence plasmid of *Escherichia coli* 0157:H7", Nucleic Acids Research (Sep. 1998) 26(18):4196–4204.*
Markino et al. "Complete nucleotide sequence of 93–kb and 3.3 kb plasmids of an enterohemorrhagic *Escherichia coli* 0157:h7 derived from Sakai outbreak", DNA research 5:1–9 (1998).*

* cited by examiner

*Primary Examiner*—Jeffrey Fredman
(74) *Attorney, Agent, or Firm*—Quarles & Brady LLP

(57) ABSTRACT

The entire genome of pathogenic *E. coli* strain 0157:H7 has been sequenced. All of the genomic DNA sequences present in 0157 and absent in the previously sequenced laboratory strain K12 are presented here.

4 Claims, No Drawings

SEQUENCES OF E. COLI O157

CROSS-REFERENCE TO RELATED APPLICATIONS

This application is a continuation of U.S. Ser. No. 09/453,702 filed Dec. 3, 1999 now U.S. Pat. No. 6,365,723 which claims priority from U.S. Provisional Patent Application No. 60/110,955 filed on Dec. 4, 1998.

STATEMENT REGARDING FEDERALLY SPONSORED RESEARCH OR DEVELOPMENT

This invention was made with United States government support awarded by NIH-A141329. The United States has certain rights in this invention.

BACKGROUND OF THE INVENTION

*Escherichia coli* is a common enteric bacterial strain that has both laboratory and human health importance. One particular strain of *E. coli* designated O157:H7 is a human enteric pathogen that causes acute hemorrhagic colitis. Young children and the elderly are particularly susceptible to disease caused by this bacteria, which is usually contracted by eating contaminated food such as undercooked meat. In the most vulnerable patients, the colitis frequently develops into hemolytic uremic syndrome (HUS), a condition that is often fatal. The disease has a very rapid progression, and is consequently very difficult to treat. Often, patients are severely ill by the time the disease is diagnosed. Once a diagnosis has been made, appropriate antibiotics may be administered to kill the infective bacteria. Sometimes, however, by the time a diagnosis has been rendered, toxic proteins secreted by the bacteria have damaged mucosal cells and entered the blood stream. Recently, clinical isolates of O157:H7 have been found to exhibit resistance to an increasing spectrum of antibiotics, which will further complicate treatment.

The source of the bacteria in the several recent cases of disease caused by this organism were traced to hamburgers purchased in fast food restaurants. The bacteria are extremely proficient at establishing an infection; ingestion of as few as 10 live bacteria is sufficient to establish an infection. The highly infective nature of O157:H7 and the devastating sequelae associated with infection by this bacteria, together with the extensive public attention given to outbreaks of hemorrhagic colitis, has generated a great deal of interest among medical professionals and the general public in developing the means for early diagnosis and treatment of the disease. Farmers are desirous of an effective treatment of infections in cattle and pigs, which are the main reservoirs for *E. coli* enteric pathogens. The ability to diagnose and treat livestock infected by this organism will prevent the loss of livestock and the transmission of the organism from animals to humans. Meat suppliers and those in the food industry are very much interested in a means for detecting the organism in tainted meat. Because the infective dose of O157:H7 is extremely low, a highly sensitive test is needed to identify contaminating organisms in food.

Modern geneticists have been working to resolve the genetic code of many organisms. Efforts to sequence the human genome are ongoing. The effort to sequence the genomes of whole organisms began with an effort to sequence the genome of *E. coli*. For the original effort to sequence the *E. coli* genome, a useful and common laboratory strain, designated K12, was chosen. The entire genome of that strain was sequenced and published. *Science*, 277:1453–1462 (1997). Since the genes which are responsible for the pathogenicity of *E. coli* O157:H7 are missing from strain K12, the sequence of the K12 genome is of limited help in developing tools to detect, hinder or destroy *E. coli* O157:H7.

Some efforts have been directed toward the sequencing of specific genes from O157:H7. U.S. Pat. No. 5,798,260 describes the sequence of one specific gene, named adhesion, from that genome. The development of additional sequence information from *E. coli* O157:H7 would be needed for comprehensive efforts at detection, diagnosis, prophylaxis and therapeutic approaches to infections caused by the organism.

BRIEF SUMMARY OF THE INVENTION

It is an object of the invention to provide essentially the entire sequence of *E. coli* O157:H7 to enable detection, diagnosis, prophylaxis and therapeutic tools to combat bacterial infections.

It is another object of the present invention to provide a means to detect low numbers of *Escherichia coli* O157:H7 in a contaminated food source.

It is yet another object of this invention to provide a means for the early diagnosis of humans and livestock infected with O157:H7.

Another object of the present invention is to provide a means of treating humans and livestock infected with O157:H7.

It is a further object of the present invention to provide a means for the prevention of infection by O157:H7.

The present invention includes many DNA sequences that are unique to *E. coli* O157:H7.

One aspect of the present invention is a DNA sequence comprising an open reading frame (ORF), designated 03169, that encodes a putative cytotoxin 3169 amino acids in length that resembles the clostridial cytotoxins ToxA and ToxB of *C. difficile* and cytotoxin L of *C. sordelli*.

Another aspect of the present invention is a DNA sequence that constitutes an urease gene cluster.

A third aspect of the present invention is a chromosomal gene that encodes a toxin related to the RTX family of cytotoxins and associated transport proteins.

Another aspect of the present invention are genes that are found in the Locus of Enterocyte Effacement (LEE), a 45-kb cluster of genes that are involved in the attachment of pathogens to intestinal epithelial cells and other related functions necessary to establish infection.

Another aspect of the present invention is a hypothetical serine/threonine kinase (stk) encoded by phage 933W, a lysogenic bacteriophage found in O157:H7.

The present invention is also a putative tail fiber gene, which is found on phage 933W.

Another aspect of the present invention is a method for detecting *E. coli* O157:H7 and distinguishing the strain from other strains of *E. coli* by genetic analysis and testing.

It is a feature of the invention disclosed here that virtually the entire genome of *E. coli* O157:H7 is set forth in the data contained here, combined with the information already published in the field.

BRIEF DESCRIPTION OF THE SEVERAL VIEWS OF THE DRAWINGS

Not applicable.

DETAILED DESCRIPTION OF THE INVENTION

The investigators here have sequenced virtually the entire genome of *E. coli* O157:H7. Presented in this specification is essentially all the DNA sequence which is contained in strain 0157:H7 and not found in the prviously sequenced *E. coli* strain K12. The genome sequence is essentially complete, lacking only an occasional presumably small sequence linkage between established long sequences known. The availability of the sequence data presented here will enable intelligent design of diagnostic detection, prophylaxis and therapeutic tools for disease and infections caused by this organisms.

The sequence of *E. coli* 0157:H7 was, in brief, performed by shotgun cloning in the M13 Janus vector (Burland et al. *Nucl. Acids Res.* 21:3385–3390 (1993)). Genomic DNA was prepared for library construction by nebulization, end-repair and size fractionation as described in Mahillon et al. *Gene* 223:47–54 (1998). Recovered DNA fragments were ligated into the M13 Janus vectors. Library subclones were picked as plaques, from which template DNAs were prepared and then sequenced by Prism-terminator Cycle Sequencing chemistry and analyzed on ABI377 automated sequencers. Sequences were assembled by the Seqman II program (DNASTAR), and finishing employed a combination of PCR and primer walking techniques. open reading frames were identified and analyzed as described in Blattner et al. *Science* 277:1453–1474 (1997). All the sequences presented in this specification are unique to strain 0157:H7 as compared to strain K12. This sequence data, when combined with the sequence of K12, resolves all of the genetic sequence of 0157:H7. The information on the K12 sequence, contained in *Science,* 277:1453–62 (1997) is hereby incorporated by reference as if set forth in full herein.

An important analysis which has been begun on this sequence data is the identification of genetic sequences associated with the pathogenesis of infection, which sequences provide information essential to the diagnosis, treatment, and prevention of infection by that organism. In order to facilitate the identification of genes involved in the pathogenesis of infection by enterohemorrhagic *E. coli* (EHEC) for use in detection of the pathogen, and in the diagnosis, treatment, and prevention of enterohemorrhagic infections, the entire genomic DNA sequence of *E. coli* 0157:H7 serovar EDL933 (ATCC 43895) was determined and compared with that of *E. coli* K-12, a nonpathogenic laboratory strain, as described in detail in the examples below.

Surprisingly, the genome of 0157:H7 was found to be more than one million base pairs larger than that of K-12 and to have up to 1000 genes not found on K-12. These additional gene sequences are distributed throughout more than 250 sites in islands, with each island containing from zero to sixty genes. An unexpected finding is that many of the new genes resemble virulence determinants from a wide variety of pathogens, ranging from *Helicobacter pylori* to *Clostridium difficile*. Numerous sequences of interest were identified in the genome of *E. coli* 0157:H7, including chromosomal, plasmid, and phage sequences.

Attached to this patent application is a sequence listing containing essentially all of the DNA sequence of the regions in the O157 genome that are not present in the K12 genome. This sequence is present in the sequence listing as SEQ ID:NO 1 through SEQ ID:NO 255. These sequences correspond to the 255 islands of O157 DNA that did are not found in K12 DNA. Each of those islands has been assigned an identification (an OZ identification, meaning in the O157 zone of the genome, as opposed to a K12 region). In the description of each of the sequences is a base pair listing of where that particular sequence is found in the underlying backbone of the entire O157 sequence.

Also included in this patent application are two tables intended to make available some of the genetic analysis which has been done on these sequences. Table 1 simply itemizes the 0157 islands by OZ number and lists some of the presently known noteworthy features in the sequenced islands. Table 2 is a listing of the open reading frames (ORFs) identified in each of the OZ sequences. Where the open reading frames have been matched to putative function, such an indication is found matched to the open reading frame in Table 2. The protein encoding by each such ORF can be determined by appropriate conversion of the open reading frame DNA sequence to protein amino acid sequence using the genetic code.

By definition, the genetic material in the OZ sequences described here are sufficient for pathogenocity in humans, since strain O157 is highly pathogenic while K12 is not. In addition, analysis of the open reading frames and computer comparisons to sequences from other pathogens had allowed identification of several of the open reading frames which code for proteins specifically associated with pathogenicity.

A gene encoding an unusually large ORF, designated o3169, which putatively encodes a 3169 amino acid protein, was identified on plasmid pO157, a 92 kb plasmid resident in *E. coli* O157:H7 in an autonomously replicating form. Data base searches revealed that the deduced amino acid sequence of this putative ORF is similar to the large clostridial cytotoxins, ToxA and ToxB of *C. difficile* (Dove et al., *Infect. Immun* 58:480–488 (1990); von Eichel-Streiber et al., *Mol. Gen. Genet.* 233:260–268 (1992)) and cytotoxin L of *C. sordelli* (Green et al. *Gene* 161:57–61, 1995). ToxA, ToxB, and cytotoxin L are 2710, 2366, and 2338 amino acid residues in length, respectively. The sequences of o3169 and its putative translation product are shown in SEQ ID NO:256 and SEQ ID NO:257, respectively.

The clostridial cytotoxins are homologous proteins with three domains (von Eichel-Streiber et al., *Trends in Microbiology* 4: 375–382 (1996)). The N-terminal region contains a catalytic domain, a glucosyltransferase that acts on small GTP-binding proteins to interfere with their function in the organization of cytoskeletal actin filaments (Just et al., *Nature* 375: 500–503 (1995)). The central region contains a translocation domain that directs the secretion of the toxin, and the C-terminal region contains a target binding site.

The amino acid identity between the translation product of o3169 and the known cytotoxins is relatively weak (20%) over 444 amino acids, to ToxB. However, the alignment of these sequences is striking. The region having the highest level of amino acid identity is the first (N-terminal) 700 amino acids, which corresponds to the catalytic site of the clostridial toxins.

ToxA damages intestinal mucosal cells, and when ToxA is present, ToxB gains access to the cells underlying the mucosa, causing further damage. By analogy, the putative cytotoxin encoded by o3169 may contribute to the damage to mucosal cells observed in enterohemorrhagic *E. coli* infections by acting alone or in concert with some other factor to destroy submucosal tissue, thereby causing or exacerbating the acute symptoms of infection. Therefore, the putative toxin is a promising target for treatment of persons infected by enterohemorrhagic *E. coli*. The administration of an antibody raised against the newly discovered toxin, or a portion of the toxin, could provide an effective treatment of severe symptoms of infection. The administration of the antitoxin could be used in conjunction with antibiotic therapy. Treatment with antibiotics is effective in controlling the infection itself. However, antibiotic therapy alone is ineffective in preventing or alleviating symptoms of the disease if the antibiotic is not administered in time to prevent the production of the toxin.

A cluster of seven genes very similar to the urease genes of numerous other bacterial pathogens has been identified on the chromosome of *E. coli* O157:H7 and its sequence determined (SEQ ID NO:258). Urease, or urea amidohydrolase, catalyzes the hydrolysis of urea to yield ammonia and carbamate. Expression of the urease genes in urogenital and gastroenteric bacteria is important in pathogenesis. For example, formation of ammonia by cell-surface bound urease in *Heliobacter pylori* is thought to cause a localized increase in pH allowing survival of the bacteria in the harshly acidic environment of the host's gastric system. In the gastrointestinal pathogens *Yersinia enterocolitica* and *Morganella morganii*, urease was found to be activated by low-pH conditions (Young et al., *J. Bacteriology* 178: 6487–6495 (1996)). The urease isolated from Vibrio parahaemolyticus, which causes gastroenteritis and traveler's diarrhea, has been found to cause intestinal fluid accumulation in suckling mice (Cai and Ni, *J. Clin. Lab. Analysis* 10(2): 70–73 (1996)). The presence of urea has been found to enhance intracellular survival of urease-positive Bordatella bronchiseptica, a mammalian respiratory pathogen (McMillan et al., *Microbial Pathogenesis* 21(5): 379–394 (1996)).

Gene order is conserved among most known bacterial urease clusters (Neyrolles et al., *J. Bacteriol.* 178(9): 2725 (1996)) and the urease gene cluster of *E. coli* O157:H7. The urease gene cluster begins with ureD, an accessory gene involved with regulation, followed by three structural genes, ureA, ureB, and ureC, and three accessory genes, ureE, ureF, and ureG. The latter three genes are believed to be involved in nickel metallocenter biosynthesis (Moncrief and Hausinger, *J. Bacteriol.* 178(18): 5417–5421 (1996)). In-frame stop codons prematurely terminate ureD (24 amino acids) and ureE (four amino acids) relative to the C-termini shared by most protein database entries. All 7 ORFs have from 70–96% identity to genes from *Klebsiella aerogenes* (Mulrooney and Hausinger, *J. Bacteriol.* 172(10): 5837–5843 (1990)). It is of interest that the sequence of strain EDL933 is more similar to the urease cluster of Klebsiella than that of *E. coli* strain 1440, the only other *E. coli* urease sequence presently available (D'Orazio and Collins, *J. Bacteriol.* 175(6): 1860–1864 (1993)). For example, ureD of EDL 933 is 71% identical to the corresponding gene from *Klebsiella aerogenes*, but only 47% identical to the plasmid borne ureD gene of *E. coli* 1440.

Some strains of *E. coli*, particularly the uropathogens, test positive for urease activity, but EDL933 does not. A urease-positive mutant strain of O157:H7 observed among U.S. clinical isolates (Hayes et al., *J. Clin. Microbiol.* 33(12): 3347–3348 (1995)) may reflect the activation of a cryptic operon. Alternatively, the urease-positive mutant strain of O157:H7 may reflect a regulatory change for an already functional operon. Analogously, urease-negative *Y. pestis* exhibits a urease gene complex very similar to those of urease-positive members of the Yersinia genus. (de Koning-Ward and Robins-Browne, *Gene* 182(1–2): 225–228 (1996)).

The urease gene cluster has potential utility in vaccine development. For example, the whole gene cluster could be genetically engineered into an attenuated strain to be used as a vaccine. The urease gene cluster would enhance the ability of the vaccine strain to survive the acid environment of the stomach.

An O157:H7 chromosomal gene cluster related to the RTX family of cytotoxins was identified as described in the examples below. The RTX cytotoxins are a group of exotoxins produced by Gram-negative bacteria that share the properties of secretion by a leader-independent pathway and a tandemly repeated sequence nine amino acids in length that is responsible for calcium binding (Welch et al., *FEMS Microbiol. Immunol.* 5: 29–36 (1992)). RTX toxins recognize a beta2 integrin on the surface of host cells (Lally et al., *J. Biol. Chem.* 272: 30463–30469 (1997)). Known members of the family include apxIA, apxIIA, and apxIIIA from *Actinobacillus pleuropneumoniae*, cyaA from *Bordetella pertussis*, frpA from *Neisseria meningitidis*, prtC from *Erwinia chrysanthemi*, hlyA and elyA from *Escherichia coli*, aaltA from *Actinobacillus actinomycetemcomitans*, and lktA from *Pasteurella haemolytica*. Hybridization studies using probes designed from sequences of these known toxins identified potential RTX toxin genes in several pathogenic bacterial species for which no RTX toxins were previously known, indicating that RTX or RTX-like toxins are widely distributed among pathogenic gram-negative bacteria (Kuhnert et al., *Appl. Environ. Microbiol.* 63: 2258–2265, (1997)). The novel O157:H7 toxin locus (SEQ ID NO:259 and SEQ ID NO:260) comprises three genes, including the putative toxin and two proteins involved in transport. The gene order and sizes are consistent with other RTX loci. The putative toxin gene shows only marginal similarity to other RTX toxins, and the match is limited to the glycine-rich calcium binding repeat region. The more highly conserved transport genes are approximately 40% identical to related genes found in other RTX clusters.

The Locus of Enterocyte Effacement (LEE) is a 45 kb cluster of genes involved in intimate adherence of pathogens to intestinal epithelial cells, initiation of host signal, transduction pathways, and formation of attaching and effacing lesions (McDaniel et al., *Proc. Natl. Acad. Sci.* 92: 1664–1668, (1995); McDaniel and Kaper, *Molecular Microbiology* 23: 399–407 (1997)). Colony hybridization studies indicate that sequences homologous to the entire element are found in numerous enteropathogenic *E. coli* (EPEC), enterohemorrhagic *E. coli* (EHEC), and other related bacteria (McDaniel et al., *Proc. Natl. Acad. Sci.* (1995)). The O157:H7 LEE sequence is shown in SEQ ID NO:261. Sequence data is currently available for the entire LEE from another EPEC strain E2348/69. Comparisons of the O157:H7 LEE to that of E2348/69 revealed that although many genes were nearly identical between the two strains, other genes are markedly variable. This variability is non-random with respect to gene function, in that all proteins known to be exported to the extracellular environment are variable, whereas those proteins known to constitute the secretion machinery are invariant. A similar observation has been made based on comparisons of the inv-spa complex of *Salmonella enterica* (Boyd et al. *J. Bacteriol.* 179: 1895–1991 (1997)).

Four contiguous LEE genes, L0027, L0028, L0029, and L0030, have been selected for their diagnostic potential. A comparison of these genes from EDL933 and the corresponding genes in E2348/9 revealed significant differences between the strains: L0027 (33.52% difference); L0028 (17.48%); L0029 (21.94%); and L0030 (25.30%). In E2348/69, the homolog of known L0027 is known as tir (B. Kenny et al., *Cell* 91: 511–520). The tir gene encodes a product that is translocated from the bacterium to the host cell where it serves as the receptor for intimin, another LEE encoded gene product. Little is known about the function and role in pathogenesis of the other three hypervariable virulence LEE genes. The L0028 gene product shows 27% identity with a hypothetical protein encoded in a Shigella virulence-associated cluster (Elliot et al, *Mol. Mircro.*, in press). The deduced amino acid sequence of the L0027 gene shows slight similarity to a secreted protein in the plant pathogen *Erwinia amylovora*, and the L0028 translational product has 27% identity with a hypothetical protein encoded in a Shigella virulence-associated cluster (Elliot et al. *Mol. Micro.*, in press).

The entire toxin-converting phage 933W was sequenced as described in the examples. Two novel gene sequences with potential diagnostic and therapeutic value were identified. The first is an ORF (SEQ ID NO:262) that encodes a protein (SEQ ID NO:263) that resembles members of the eukaryotic family of serine/threonine kinase (stk). The amino acid sequence similarities span the conserved regions in the catalytic domain of the eukaryotic protein kinases, including both the ATP binding and active site patterns as described in the PROSITE database. BLASTP, FASTA, and DeCypher II searches with the stk sequences all yield much higher scoring matches to the eukaryotic serine/threonine protein kinases than do searches with the YpkA protein of *Yersinia pseudotuberculosis* and *Y. enterocolitica*. There is some suggestion that the Yersinia protein kinase is involved in virulence, by interfering with the signal transduction pathway of the mammalian host, and bacteriophage 933W may interfere with the host systems in the same manner.

Shiga-like toxins, which are encoded by lysogenic bacteriophages, are considered to be one of the major pathogenic features of enterohaemorrhagic *E. coli* strains. Toxin genes have been previously sequenced in 933W. Based on the arrangement of the 933W and our knowledge of phage organization, we postulated that shiga-like toxin genes are "late genes" the expression of which is controlled by a homologue of the Q gene of bacteriophage lambda. If in fact the shiga-like toxin genes are late genes, the toxins would be expressed only during a lytic infection. Bacterial cells already carrying the prophage would be immune to super-infection by the phage released during a lytic phase of growth. However, non-lysogens in the vicinity could be infected and produce additional phage and toxin in what can be envisioned as an amplification by recruitment. Thus any late gene product could be an indicator of a condition under which toxin production would be increased. We have identified a putative tail fiber gene in the bacteriophage sequence. The coding region and the deduced amino acid sequence of the gene are shown in SEQ ID NO:264 and SEQ ID NO:265, respectively. The phage tail fibers, expressed by late genes, are required for infection of new bacterial hosts during the lytic phase of growth. Therefore, antibodies to this protein could serve as a diagnostic, as well as a therapeutic to prevent the proposed recruitment and infection of other bacterial cells.

Several other putative pathogenocity genes have been identified as well. The following is a list of additional pathogenic genes by reference to the segment (OZ number) and to the open reading frame (F0 number) in which the sequence for that pathogen gene is presented below.

Toxins
OZID_175 (F1037) homolog of Shigella SHeT
OZID_175 (F1041, F1042) putative *Clostridium difficile* ToxAB-like cytotoxin
OZID_11 (F0027) *Legionella pneumophila* IcmF-like homolog Fimbriae
Attachment to the host:
OZID_197 (F1133–F1139)
OZID_215 (F1231–F1237)
Both encode six proteins most similar to those of the lpfABCDE locus of Salmonella.

Iron Utilization
Iron is complexed in hemoglobin in the host so that infecting bacteria need efficient systems to actively acquire iron.
OZID_196 (F1124–F1132) chu locus homologous to the shu locus of *Shigella dysenteriae*
OZID_29 (F1132–F1134) homologous to the *Actinobacillus pleuropneumoniae* afuABC locus
OZID_176 (F1054–1059) a putative siderophore receptor and associated proteins plus one hypothetical protein, similar to FecD, FecC (both permeases) and FecE (ATP-binding protein) of Synechocystis.
OZID_78 (F0527 F0528), tonB-dependent outer membrane receptor, and ABC transporter
OZID_59 (F0294) putative exogenous ferric siderophore receptor similar to R4
OZID_62 (F0360) Salmonella IroE-like protein, Phage Encoded
OZID_98 (F0630) and OZID_139 (F0825), putative superoxide dismutases, potentially giving protection from oxidative stress Metabolic Capabilities
These may contribute to the ability to grow in the intestinal environment.
OZID_26 (F0125–F0131) high affinity ribose transport system
OZID_29 (F0135–F0137) hexose-phosphate transport
OZID_49 (F0167–F0179) includes glutamate fermentation, fumarase, ATP-transferase
OZID_59 (F0256–F0262) urease
OZID_62 (F0394–F0409) fatty acid/polyketide biosynthesis, interspersed unknowns
OZID_151 (F0921–F0925) sucrose utilization, D-serine permease part of 12 kb island
OZID_156 (F0932–F0934) DMSO reductase-anaerobic
OZID_193 (F1097–F1113) fatty acid biosynthesis
OZID_194 (F1115–F1123) PTS and sugar modification enzymes, substrate unknown
OZID_232 (F1266–F1272) PTS sorbose
OZID_233 (F1274–F1282) sugar (ribose) transport, modification One wishing to practice the present invention using one of the disclosed sequences could do so by isolating the sequence from ATCC 43895 using knowledge of the nucleotide sequence and standard methods known to one of skill in the art.

It is expected that minor sequence variations in *E. coli* O157:H7-specific nucleotide sequences associated with nucleotide additions, deletions, and mutations, whether naturally occurring or introduced in vitro, would not interfere with the usefulness of these sequences in the detection of enterohemorrhagic *E. coli*, in methods for preventing EHEC infection, and in methods for treating EHEC infection. Therefore, the scope of the present invention is intended to encompass minor variations in the claimed sequences.

By an *E. coli* O157:H7-specific nucleotide probe it is meant a sequence that is able to hybridize to *E. coli* O157:H7 target DNA present in a sample containing *E. coli* O157:H7 under suitable hybridization conditions and which does not hybridize with DNA from other *E. coli* strains or from other bacterial species. It is well within the ability of one skilled in the art to determine suitable hybridization conditions based on probe length, G+C content, and the degree of stringency required for a particular application.

The probe may be RNA or DNA. Depending on the detection means employed, the probe may be unlabeled, radiolabeled, or labeled with a dye. The probe may be hybridized with a sample that has been immobilized on a solid support such as nitrocellulose or a nylon membrane, or the probe may be immobilized on a solid support, such as a silicon chip.

The sample to be tested may include blood, urine, feces, or other materials from a human or a livestock animal. Alternatively, the sample may include food intended for human consumption. The sample may be tested directly, or may be treated in some manner prior to testing. For example, the sample may be subjected to PCR amplification using appropriate oligonucleotide primers.

Any means of detecting DNA-RNA or DNA-DNA hybridization known to the art may be used in the present invention.

Also presented in this specification is a series of sequence listings constituting the entire sequence of all portions of the genome of *E. coli* O157:H7 that do not appear in strain K12. These sequences are presented as SEQ:ID:NO:1 to SEQ:ID:NO:255 below. Since all of these sequences are diagnostic of 0157:H7, as compared to K12, sequence information from any of these sequences can be used to design diagnostic probes useful to distinguish strain 0157:H7 from strain K12 using molecular techniques. To have reasonable assurance of success under conditions of variable stringency, it is preferred that such diagnostic probes use sequences which are at least 25 nucleotides or longer in length. Any 25-mer selected from amongst any of the sequences in any of SEQ:ID:NO:1 through SEQ:ID:NO:255 may be used for such a probe.

EXAMPLES
Isolation and Cloning of DNA

A 45-Kb LEE was isolated from EDL933, an EHEC 0157:H7 serovar, using a homologous recombination driven targeting vector (Posfai et al. *J. Bacteriol.* 179: 4426–4428 (1997)). Briefly, a targeting vector, loaded with known chromosomal sequence flanking LEE, was used to introduce novel flp recombinase target sites by homologous recombination. Expression of flp from a helper plasmid promotes excision of the target as a small plasmid. The excised plasmid DNA was shotgun cloned into the Janus M13 vector (Burland et al., *Nucleic Acids Res.* 21:3385–3390 (1993)). The urease gene cluster and the RTX toxin locus were isolated and cloned in the same manner as LEE (Posfai et al. *J. Bacteriol.* 179:4426–4428 (1997)).

Phage 933W obtained from the supernatant of a liquid culture of *E. coli* O157:H7 serovar EDL933 was used to infect *E. coli* K-12 strain LE392 in liquid culture. Phage were propagated in *E. coli* K-12 strain LE392 and isolated using standard methods. Purifying the phage by standard methods including a CsCl-EtBr density gradient centrifugation step, and isolating the viral DNA. The viral DNA was sheared by nebulization and shotgun cloned into the Janus M13 vector.

The plasmid pO157 was isolated from *E. coli* O157:H7 EDL933W using standard methods known to the art. The plasmid was shotgun cloned into the Janus M13 vector.

Total genomic DNA from *E. coli* O157:H7 EDL933 was shotgun cloned into the Janus M13 vector.

DNA Sequence Determination and Analysis

Random shotgun cloning of total genomic DNA into the Janus M13 vector (Burland et al., *Nucleic Acids Res.* 21: 3385–3390 (1993)) provided template for automated sequencing using dye-terminator chemistry. A sufficient number of random clones was sequenced to provide 6x coverage of each element with a minimum quality of 2x coverage, including both strands, for all regions. The sequences were assembled using SeqManII (DNASTAR) and edited manually.

Open reading frames were located with GeneQuest (DNASTAR) using both *E. coli* and phage trained matrices and annotated based on protein sequence searches (DeCypherII Hardware/software System, TimeLogic, Inc.). All sequence alignments were performed using MegAlign or Align (DNASTAR) and levels of divergence were assessed with the Molecular Evolutionary Genetic Analysis (MEGA) software package (Kumar et al., *MEGA: Molecular evolutionary genetics analysis*. The Pennsylvania State University, University Park (1993)). The Codon Adaptation Index (CAI) was calculated by the method of Sharp and Li (*Nucleic Acids Res.* 15(3): 1281–1295 (1987)).

TABLE 1

| Sequence_ID | Length (bp) | Description |
|---|---|---|
| OZID_1 | 6506 | putative outer membrane protein, usher and chaperone, possibly fimbrial |
| OZID_2 | 41 | small (41 bp) no features |
| OZID_3 | 635 | topoisomerase toxin-antitoxin system |
| OZID_4 | 1010 | unknown |
| OZID_5 | 35 | small (35 bp) no features |
| OZID_6 | 30 | small (30 bp) no features |
| OZID_7 | 9381 | putative fimbrial biosynthesis cluster homologous to K-12 but highly divergent |
| OZID_8 | 32 | small (32 bp), no features |
| OZID_9 | 124 | unknown, no ORFs |
| OZID_10 | 221 | yafE, putative enzyme |
| OZID_11 | 31960 | many unknowns, putative macrophage toxin, clpB paralog, and rhsG |
| OZID_12 | 3660 | rhs element |
| OZID_13 | 10523 | lambdoid prophage integrated downstream of tRNA-thrW |
| OZID_14 | 12886 | P4-like prophage integrated downstream of tRNA-thrW |
| OZID_15 | 6133 | unknowns including 3 orfs similar to cluster (orf2, orf3, opdE) implicated in regulation of a Pseudomonas aeruginosa porin for imipenem/basic amino acid uptake, begins within B0282-yagP, putative regulator |

TABLE 1-continued

| Sequence_ID | Length (bp) | Description |
|---|---|---|
| OZID_16 | 2450 | ISEc8 plus 8bp duplicated target site |
| OZID_17 | 4716 | several oxidoreductases, unknowns and a transcriptional regulator |
| OZID_18 | 3695 | extends C-terminus of eaeH creating a much longer putative adhesin similar to intimin of the LEE of this organism and invasins of Yersinia, extends C-terminus of ykgA, putative regulator |
| OZID_19 | 589 | putative dehydrogenase (partial) |
| OZID_20 | 100 | putative dehydrogenase (partial) |
| OZID_21 | 4998 | unknowns including putative broken recombinase and possible invertible region |
| OZID_22 | 4643 | putative secreted protein similar to AIDA-1 (diffuse adherence in DAEC 2787) and transport protein |
| OZID_23 | 94 | REP region |
| OZID_24 | 93 | no features |
| OZID_25 | 598 | unknowns |
| OZID_26 | 4588 | putative sugar (possibly ribose) transport system |
| OZID_27 | 565 | spanned by REP region |
| OZID_28 | 1834 | putative regulator and unknown |
| OZID_29 | 8114 | ferric iron uptake system similar to afuABC of Actinobacillus and two component regulatory system similar to uhpABC which is involved with hexose phosphate transport |
| OZID_30 | 1394 | putative structural protein created by merging 5' end of B0371-yaiT and B0374-yaiU |
| OZID_31 | 45 | small (45 bp) |
| OZID_32 | 1939 | creates alternate N-ter (much longer reading frame) for K-12 orf B0392, unknown |
| OZID_33 | 372 | unknown |
| OZID_34 | 1650 | unknown |
| OZID_35 | 687 | unknowns similar to unknowns found in Yersinia and Mycobacterium |
| OZID_36 | 1983 | unknown |
| OZID_37 | 39 | small (39 bp) no features |
| OZID_38 | 53 | small (53 bp), no annotated features |
| OZID_39 | 25165 | putative novel RTX-like exoprotein and transport system |
| OZID_40 | 2643 | unknowns, REP region |
| OZID_42 | 29 | REP region |
| OZID_43 | 11613 | novel Rhs element |
| OZID_44 | 491 | largely a tandem repeat of preceding 468 bp (one copy in K-12 and it is disrupted by IS186) |
| OZID_45 | 30 | small (30 bp) no features |
| OZID_46 | 520 | IRU with 69 bp deletion in center |
| OZID_47 | 1403 | small unknowns |
| OZID_48 | 70 | small (70 bp), no annotated features |
| OZID_49 | 13965 | putative glutamate uptake and fermentation system plus several unknowns |
| OZID_50 | 49 | small (49 bp) no features |
| OZID_52 | 38577 | lambdoid prophage |
| OZID_53 | 2807 | unknowns |
| OZID_54 | 103 | internal segment of unknown, REP region |
| OZID_55 | 996 | 2 unknowns |
| OZID_56 | 3515 | unknowns and putative sulfatase |
| OZID_57 | 2561 | 2 unknowns |
| OZID_58 | 349 | unknown |
| OZID_59 | 87563 | 3' end of serW; integrase, urease, tellurite resistance, complement resistance, diacylglycerol kinase, colicin immunity, secreted proteins, outer membrane receptor, DNA repair, CP4-like prophage ORFs, unknowns; IS cluster, partials, ISEc8, IS629, IS1A |
| OZID_60 | 40 | 39 bp insertion in ftsK leading to 13 aa insertion in a glutamine and proline rich repetitive region |
| OZID_61 | 40 | small (40 bp), no annotated features |
| OZID_62 | 49795 | putative lambdoid phage beginning in 3' end of serT tRNA includes some genes similar to database entries: integrase, unknowns, division inhibition protein, lambdoid phage lysis genes, regulator. Partial IS elements, enterotoxin EAST1, IS629 with deletion |
| OZID_63 | 2512 | continued from the end of previous contig |
| OZID_64 | 61658 | 933W, fully described in Plunkett et al., J. Bacteriol. 181:1767–1778 (1999) |

TABLE 1-continued

| Sequence_ID | Length (bp) | Description |
|---|---|---|
| OZID_65 | 2499 | unknown |
| OZID_66 | 31728 | large cluster including many unknowns, a pilin-like structural subunit and chaperone, putative secreted protein, HecB-like protein and several genes encoding components of a fatty acid or polyketide biosynthesis system |
| OZID_67 | 988 | no annotated features |
| OZID_68 | 9827 | no annotated features |
| OZID_69 | 1411 | 2 genes similar to elements of the 933L, the cryptic P4-family prophage in the LEE |
| OZID_70 | 104 | REP region |
| OZID_71 | 26173 | lambdoid prophage with a broken integrase similar to e14 and P21, also sporadic matches to other E. coli phage, including 933W |
| OZID_72 | 3191 | IS2 and IS285 partials, unknown orfs |
| OZID_73 | 15472 | lambdoid prophage with Salmonella-like integrase, sporadic matches to other coli phage, Streptomyces phi-C31 and Bacillus phi-105, REP region |
| OZID_74 | 46819 | lambdoid prophage with P21-like integrase and excisionase, and very lambda-like structural genes; IS629 with deletion |
| OZID_75 | 33 | small (33 bp), no annotated features |
| OZID_76 | 92 | no annotated features |
| OZID_77 | 1313 | IS629 is entire segment |
| OZID_78 | 6737 | TonB dependent outer membrane receptor, molybdenum and/or iron transport proteins, and several unknowns |
| OZID_79 | 75 | no annotated features |
| OZID_80 | 41 | no features |
| OZID_81 | 38276 | lambdoid prophage with P21-like integrase, sporadic matches to various E. coli and B. subtilis phage, lambda-like tail components, a partial tonB paralog, and many unknowns |
| OZID_82 | 354 | no annotated features |
| OZID_83 | 205 | unknown |
| OZID_84 | 1494 | unknowns |
| OZID_85 | 498 | extends N-terminus of K-12 hypothetical B1522 |
| OZID_86 | 124 | unknown |
| OZID_87 | 3281 | putative fimbrial genes including an usher, chaperone and structural subunit |
| OZID_88 | 1548 | 1 unknown and 2 orfs similar to bacteriophage PA-2 |
| OZID_89 | 653 | within a K-12 putative glycoprotein (B1471) |
| OZID_90 | 33 | rhs element |
| OZID_91 | 1206 | rhs element, partial IS1N |
| OZID_92 | 4447 | rhs element |
| OZID_93 | 1813 | unknowns |
| OZID_94 | 32 | small (32 bp) no features |
| OZID_95 | 4268 | unknowns most similar to a broken K-12 gene (ydbA=rtoA) in the replaced region, possibly hypervariable with a duplication, but lacking an IS2-IS30 hybrid; REP region |
| OZID_96 | 3404 | unknowns |
| OZID_97 | 101 | no features |
| OZID_98 | 34063 | lambdoid phage with many unknowns, mixed matches to E. coli phage including 933W, H-19B, N15, P21, and very lamda-like tail components, IS629 |
| OZID_99 | 494 | unknown |
| OZID_100 | 873 | two orfs similar to cI and cro of bacteriophage HK022 |
| OZID_101 | 1313 | IS629 is whole segment |
| OZID_102 | 883 | unknowns |
| OZID_103 | 665 | unknown |
| OZID_104 | 7886 | putative drug resistance efflux pump |
| OZID_105 | 3983 | chaperone protein, IS630 partial |
| OZID_106 | 6232 | putative phage components and unknown orfs |
| OZID_107 | 1711 | unknown orfs |
| OZID_108 | 44 | no annotated features; 44 bp |
| OZID_109 | 841 | unknown orf |
| OZID_110 | 1314 | IS629 |
| OZID_111 | 225 | 225 bp; no features |
| OZID_112 | 102 | 102 bp; no features |

TABLE 1-continued

| Sequence_ID | Length (bp) | Description |
|---|---|---|
| OZID_113 | 21119 | HP1/S2 integrase; phage regulator and replication proteins, partition genes, P2 tail fiber components, IS30 and IS629 partials |
| OZID_114 | 931 | part of flagellin |
| OZID_115 | 1958 | orf similar to YopM of Y. enterocolitica |
| OZID_116 | 62 | small (62 bp) no features |
| OZID_117 | 38 | small (38 bp) no features |
| OZID_118 | 45175 | lambdoid phage components lom, tail fiber, regulators, and integrase. Contains ClpP peptidase, cell division regulator, unknown orfs, IS629, 4 REP regions |
| OZID_119 | 906 | part of K-12 largest ORF |
| OZID_120 | 2448 | ISEc8 |
| OZID_121 | 3275 | unknowns, IS629 |
| OZID_122 | 210 | unknowns |
| OZID_123 | 14187 | complete O157 O-antigen biosynthesis cluster |
| OZID_124 | 1376 | putative UDP-galactose 4-epimerase |
| OZID_125 | 88 | 88 bp; no annotated features |
| OZID_126 | 745 | bacteriophage N15 gp49; putative regulator |
| OZID_127 | 328 | 328 bp; no annotated features |
| OZID_128 | 2272 | unknowns |
| OZID_129 | 30 | small (30 bp) no features |
| OZID_130 | 958 | putative fimbrial component; hypervariable homolog of yehA |
| OZID_131 | 69 | no features |
| OZID_132 | 26 | small (26 bp) no features |
| OZID_133 | 30 | small (30 bp) no features |
| OZID_134 | 3823 | putative regulator of molybdate metabolism |
| OZID_135 | 1304 | putative regulator of molybdate metabolism |
| OZID_136 | 935 | unknowns |
| OZID_137 | 1313 | IS629 |
| OZID_138 | 25 | small (25 bp) no features |
| OZID_139 | 48907 | Lambdoid phage components lom, putative prophage components; phage contains Shiga toxin SLT1a and b subunits, Q regulator and putative superoxide dimutase; putative CTX putative proteases, ISEc8, unknowns, integrase, REP region |
| OZID_140 | 41 | 40 bp; no annotated features |
| OZID_141 | 377 | unknown |
| OZID_142 | 6185 | aromatic degradation cluster; LYS-R-type regulator, partial BoxC repeat |
| OZID_143 | 150 | 150 bp; no annotated features |
| OZID_144 | 1879 | putative antibiotic efflux protein |
| OZID_145 | 1713 | unknown |
| OZID_146 | 36 | small (36 bp) no features |
| OZID_147 | 207 | partial RSA repeat |
| OZID_148 | 182 | unknown, spanned by REP region |
| OZID_149 | 7198 | unknowns; begin hypervariable fimbrial subunits, chaperone and ushers |
| OZID_150 | 186 | part of unknown ORF |
| OZID_151 | 12804 | bacteriophage P22 gp7 and 14; unknowns; putative resolvase; sucrose permease, hydrolase and regulator, fructokinase. |
| OZID_152 | 1748 | ISEco1253 is entire segment |
| OZID_153 | 396 | unknowns |
| OZID_154 | 35 | small (35 bp) no features |
| OZID_155 | 48 | small (48 bp) no features |
| OZID_156 | 4859 | DMSO reductase subunits |
| OZID_157 | 42 | part of unknown ORF |
| OZID_158 | 132 | putative ATP synthase beta subunit |
| OZID_159 | 4190 | unknowns; putative chaperone |
| OZID_160 | 17136 | unknowns; lambdoid bacteriophage components Rz, R, antirepressor, Q, nin, lambdoid unknowns, IS30 and IS911 partials, integrase, REP region |
| OZID_161 | 2077 | putative regulator; unknown |
| OZID_162 | 40 | small (40 bp) no features |
| OZID_163 | 2936 | unknowns; putative decarboxylase, putative regulator |
| OZID_164 | 9179 | Beginning of series of unknowns similar to K-12 counterparts: hypervariable; 3 iap repeats |
| OZID_165 | 32 | small (32 bp) no features |
| OZID_166 | 3487 | unknowns |
| OZID_167 | 236 | unknown |

TABLE 1-continued

| Sequence_ID | Length (bp) | Description |
|---|---|---|
| OZID_168 | 16950 | large cluster encoding a putative type III secretion system, response regulator for 2 component system, InvF-like and putative secreted proteins, and a putative lipoprotein |
| OZID_169 | 78 | part of a putative lipoprotein |
| OZID_170 | 80 | no features |
| OZID_171 | 395 | part of a putative D-3 phosphoglycerate dehydrogenase |
| OZID_172 | 3267 | unknowns; putative ATP-binding components of ABC transport system; part of a putative kinase |
| OZID_173 | 935 | unknown |
| OZID_174 | 87 | 87 bp; REP region |
| OZID_175 | 23451 | putative P4-type integrase; putative enterotoxin, cytotoxin and PagC-like virulence factors; ISEc8 complex cluster; IS2, IS1N, ISEc8, IS630 partials; IS629; ISEc8, IS3 and 1S911 partials |
| OZID_176 | 7304 | putative iron compound transport system, REP region |
| OZID_177 | 62 | 62 bp; no annotated features |
| OZID_178 | 375 | not annotated |
| OZID_179 | 100 | REP region |
| OZID_180 | 28 | small (28 bp) no features |
| OZID_181 | 2326 | PTS subunits |
| OZID_182 | 1307 | unknowns; IS629; N-terminus of a putative fimbrial protein |
| OZID_183 | 54 | no features |
| OZID_184 | 53 | small (53 bp) no features |
| OZID_185 | 674 | not annotated |
| OZID_186 | 73 | no features |
| OZID_187 | 889 | unknowns |
| OZID_188 | 2906 | unknowns |
| OZID_189 | 3511 | unknowns; helicase (3 ORFs) |
| OZID_190 | 1819 | unknowns |
| OZID_191 | 1041 | unknowns |
| OZID_192 | 943 | unknowns |
| OZID_193 | 15393 | unknowns; putative enzymes of fatty acid biosynthesis (acyl carriers, synthases and reductase); unclassified putative enzymes |
| OZID_194 | 6563 | unknowns; putative PTS subunits; putative xylulose kinase, putative phosphocarrier; putative aldolase |
| OZID_195 | 25 | small (25 bp) no features |
| OZID_196 | 9057 | heme/hemoglobin uptake system homologous to the Shu system of Shigella dysenteriae |
| OZID_197 | 5903 | putative long polar fimbrial subunits, usher and chaperone |
| OZID_198 | 39 | small (39 bp) no features |
| OZID_199 | 4021 | putative regulator, putative permease, unknown |
| OZID_200 | 217 | C-termini of an unknown and a putative outer membrane protein |
| OZID_201 | 1368 | unknown |
| OZID_202 | 6091 | unknown; putative adhesin |
| OZID_203 | 5407 | putative LPS biosynthesis enzymes |
| OZID_204 | 39 | small (39 bp) no features |
| OZID_205 | 62 | small (62 bp) no features |
| OZID_206 | 140 | hypervariable |
| OZID_207 | 857 | unknown |
| OZID_208 | 43418 | LEE element; fully described in Perna et al., Infection and Immunity 66: 3810–3817 (1998) |
| OZID_209 | 840 | unknowns |
| OZID_210 | 3357 | unknowns |
| OZID_211 | 508 | part of putative 6-phospho-beta-glucosidase |
| OZID_212 | 2625 | unknowns |
| OZID_213 | 27 | small (27 bp) no features |
| OZID_214 | 7425 | unknowns, REP region |
| OZID_215 | 6943 | putative lpf-like fimbrial subunits, usher and chaperones |
| OZID_216 | 1003 | unknowns, REP region overlaps left end |
| OZID_217 | 2692 | unknowns |
| OZID_218 | 48 | small (48 bp) no features |
| OZID_219 | 38 | small (38 bp) no features |
| OZID_220 | 34 | 34 bp; REP region |
| OZID_221 | 48 | 48 bp, no features |
| OZID_222 | 989 | unknown |
| OZID_223 | 46 | 46 bp; no features |
| OZID_224 | 2047 | unknowns |

TABLE 1-continued

| Sequence_ID | Length (bp) | Description |
|---|---|---|
| OZID_225 | 1751 | putative glycoporin |
| OZID_226 | 136 | REP region |
| OZID_227 | 1522 | unknowns |
| OZID_228 | 5519 | RHS core; unknowns; partial ISN1 |
| OZID_229 | 2691 | putative hippuricase, putative citrate permease |
| OZID_230 | 131 | hypervariable |
| OZID_231 | 107 | REP region |
| OZID_232 | 6318 | putative PTS for sorbose |
| OZID_233 | 9306 | putative response regulator, putative aldolase, putative ABC transport system for ribose, putative histidine kinase |
| OZID_234 | 164 | no features |
| OZID_235 | 1748 | ISEco1253, no other features |
| OZID_236 | 26 | small (26 bp) no features |
| OZID_237 | 46 | no features |
| OZID_238 | 32 | small (32 bp) no features |
| OZID_239 | 29 | small (29 bp) no features |
| OZID_240 | 194 | unknown, spanned by REP region |
| OZID_241 | 90 | no features |
| OZID_242 | 10236 | IS629; unknowns; putative resolvase; partial IS1351 |
| OZID_243 | 1089 | no features |
| OZID_244 | 31880 | unknowns; putative helicases |
| OZID_245 | 5629 | putative invasin |
| OZID_246 | 2797 | unknowns |
| OZID_247 | 25 | small (25 bp) no features |
| OZID_248 | 2235 | conserved unknowns |
| OZID_249 | 7808 | putative restriction/modification system; conserved unknowns |
| OZID_250 | 822 | unknown |
| OZID_251 | 53 | small (53 bp) no features |
| OZID_252 | 287 | unknown |
| OZID_253 | 22306 | unplaced contig; putative phage components |
| OZID_254 | 12848 | unplaced contig; putative phage components and unknown orfs |
| OZID_255 | 5836 | unplaced contig; phage components |
| OZID_256 | 11481 | unplaced contig; phage components |
| OZID_257 | 4229 | unplaced contig, putative phage components and unknown orfs |

TABLE 2

| Sequence_ID | Orf_ID | Orf_Start | Orf_End | Description |
|---|---|---|---|---|
| OZID_1 | F0003 | 823 | 497 | |
| OZID_1 | F0004 | 3286 | 836 | putative usher protein |
| OZID_1 | F0005 | 3982 | 3299 | putative chaperone protein |
| OZID_1 | F0006 | 4526 | 4032 | putative fimbrial subunit-like structural protein |
| OZID_1 | F0007 | 6288 | 4867 | |
| OZID_100 | F0579 | 289 | 744 | |
| OZID_101 | F0578 | 55 | 381 | unknown in IS |
| OZID_101 | F0577 | 378 | 1268 | putative transposase |
| OZID_102 | F0575 | 346 | 873 | |
| OZID_104 | F0573 | 1208 | 45 | putative transmembrane protein |
| OZID_104 | F0572 | 2590 | 1217 | putative outer membrane channel protein |
| OZID_104 | F0571 | 5696 | 2613 | putative efflux pump |
| OZID_104 | F0570 | 6850 | 5696 | putative efflux pump |
| OZID_104 | F0569 | 7631 | 6966 | putative transcriptional repressor |
| OZID_105 | F0568 | 3882 | 3292 | putative chaperone |
| OZID_106 | F1382 | 1086 | 442 | |
| OZID_106 | F1381 | 1478 | 1083 | |
| OZID_106 | F1380 | 2162 | 1494 | |
| OZID_106 | F1379 | 2263 | 2084 | |
| OZID_106 | F1378 | 3029 | 2289 | |
| OZID_106 | F1377 | 4013 | 3036 | |
| OZID_106 | F1376 | 4446 | 4021 | |
| OZID_106 | F1375 | 4780 | 5214 | |
| OZID_106 | F1374 | 5181 | 5426 | |
| OZID_107 | F0664 | 153 | 1232 | |

TABLE 2-continued

| Sequence_ID | Orf_ID | Orf_Start | Orf_End | Description |
| --- | --- | --- | --- | --- |
| OZID_107 | F0665 | 1305 | 1556 | |
| OZID_11 | F0021 | 620 | 324 | |
| OZID_11 | F0022 | 1066 | 617 | |
| OZID_11 | F0023 | 1665 | 1069 | |
| OZID_11 | F0024 | 2007 | 1744 | |
| OZID_11 | F0025 | 2465 | 1986 | |
| OZID_11 | F0026 | 3930 | 2431 | |
| OZID_11 | F0027 | 7147 | 3851 | |
| OZID_11 | F0028 | 8216 | 7422 | |
| OZID_11 | F0029 | 8833 | 8213 | |
| OZID_11 | F0030 | 9581 | 8838 | |
| OZID_11 | F0031 | 12349 | 9578 | putative protease |
| OZID_11 | F0032 | 13119 | 12358 | |
| OZID_11 | F0034 | 14455 | 13124 | |
| OZID_11 | F0035 | 14955 | 14458 | |
| OZID_11 | F0036 | 16259 | 14979 | |
| OZID_11 | F0037 | 17372 | 16284 | |
| OZID_11 | F0038 | 19180 | 17330 | |
| OZID_11 | F0039 | 19597 | 19184 | |
| OZID_11 | F0040 | 21079 | 19688 | |
| OZID_11 | F0041 | 21354 | 21130 | |
| OZID_11 | F0042 | 21889 | 21389 | |
| OZID_11 | F0043 | 22586 | 23104 | |
| OZID_11 | F0044 | 23314 | 25455 | |
| OZID_11 | F0045 | 25531 | 29745 | |
| OZID_11 | F0046 | 29748 | 30359 | |
| OZID_11 | F0047 | 30698 | 30997 | |
| OZID_110 | F0667 | 53 | 379 | orf; conserved hypothetical protein in IS |
| OZID_113 | F0670 | 381 | 106 | integrase (partial, C-terminus) |
| OZID_113 | F0671 | 1106 | 282 | integrase (partial, N-terminus) |
| OZID_113 | F0672 | 1459 | 1112 | |
| OZID_113 | F0673 | 2139 | 1489 | |
| OZID_113 | F0674 | 2559 | 2155 | putative phage-related repressor |
| OZID_113 | F0675 | 2635 | 2841 | |
| OZID_113 | F0676 | 2858 | 3061 | putative phage related regulator |
| OZID_113 | F0677 | 3083 | 3433 | peptidase |
| OZID_113 | F0678 | 3444 | 3722 | |
| OZID_113 | F0679 | 3734 | 3976 | |
| OZID_113 | F0680 | 4179 | 4595 | |
| OZID_113 | F0681 | 4619 | 4822 | |
| OZID_113 | F0682 | 4819 | 5085 | |
| OZID_113 | F0683 | 5082 | 5381 | |
| OZID_113 | F0684 | 5393 | 6010 | |
| OZID_113 | F0685 | 5704 | 5934 | |
| OZID_113 | F0686 | 6007 | 6372 | |
| OZID_113 | F0687 | 6379 | 9201 | putative phage replication protein |
| OZID_113 | F0688 | 9278 | 10237 | putative partition protein |
| OZID_113 | F0689 | 10242 | 10556 | putative partition protein |
| OZID_113 | F0690 | 11265 | 10576 | IS629 transposase |
| OZID_113 | F0691 | 11591 | 11265 | ori; hypothetical protein conserved in several IS elements |
| OZID_113 | F0692 | 11762 | 12178 | phage morphogenesis protein |
| OZID_113 | F0694 | 12157 | 12477 | |
| OZID_113 | F0693 | 12173 | 11889 | |
| OZID_113 | F0695 | 12827 | 12222 | acetlytransferase |
| OZID_113 | F0696 | 13445 | 12951 | putative phage tail fiber protein |
| OZID_113 | F0697 | 14288 | 13452 | |
| OZID_113 | F0698 | 16291 | 14165 | putative tail fiber component |
| OZID_113 | F0699 | 16397 | 16242 | putative tail fiber protein component |
| OZID_113 | F0700 | 16771 | 16406 | putative tail fiber component |
| OZID_113 | F0701 | 17338 | 16826 | putative tail fiber component |
| OZID_113 | F0702 | 18522 | 17338 | putative tail fiber component |
| OZID_113 | F0703 | 18548 | 19003 | |
| OZID_113 | F0704 | 20144 | 18954 | IS30 transposase |
| OZID_113 | F0705 | 20636 | 20244 | |
| OZID_113 | F0706 | 20866 | 21117 | |
| OZID_118 | F0709 | 505 | 1158 | |
| OZID_118 | F0710 | 1483 | 2637 | |
| OZID_118 | F0711 | 4353 | 3034 | |
| OZID_118 | F0712 | 5011 | 4412 | membrane protein |
| OZID_118 | F0713 | 7505 | 5079 | phage tail protein |
| OZID_118 | F0714 | 8557 | 7382 | phage tail protein |
| OZID_118 | F0715 | 9475 | 8798 | phage tail protein |
| OZID_118 | F0717 | 10116 | 9373 | phage tail protein |

TABLE 2-continued

| Sequence_ID | Orf_ID | Orf_Start | Orf_End | Description |
|---|---|---|---|---|
| OZID_118 | F1425 | 10304 | 10284 | |
| OZID_118 | F0718 | 10825 | 10127 | phage tail protein |
| OZID_118 | F0719 | 11154 | 10825 | phage tail protein |
| OZID_118 | F0720 | 11825 | 11151 | phage tail protein |
| OZID_118 | F0721 | 13806 | 11758 | phage tail protein |
| OZID_118 | F0722 | 14149 | 13841 | phage tail protein |
| OZID_118 | F0723 | 14472 | 14176 | phage tail protein |
| OZID_118 | F0724 | 15366 | 14614 | phage tail protein |
| OZID_118 | F0725 | 15772 | 15374 | phage tail protein |
| OZID_118 | F0726 | 16414 | 15785 | phage tail protein |
| OZID_118 | F0727 | 16692 | 16411 | |
| OZID_118 | F0728 | 17011 | 16685 | |
| OZID_118 | F0729 | 18139 | 17099 | |
| OZID_118 | F0730 | 18261 | 18587 | on; hypothetical protein in IS |
| OZID_118 | F0804 | 18584 | 19474 | IS629 transposase |
| OZID_118 | F0732 | 19440 | 19631 | |
| OZID_118 | F0733 | 20583 | 19477 | putative peptidase |
| OZID_118 | F0734 | 21883 | 20381 | |
| OZID_118 | F0735 | 22044 | 21883 | |
| OZID_118 | F0736 | 24215 | 22092 | |
| OZID_118 | F0737 | 24688 | 24212 | |
| OZID_118 | F0738 | 25610 | 25143 | cell lysis protein |
| OZID_118 | F0739 | 26333 | 25764 | antirepressor |
| OZID_118 | F0740 | 27137 | 26604 | cell lysis protein |
| OZID_118 | F0741 | 27535 | 27188 | |
| OZID_118 | F0742 | 27857 | 27537 | cell lysis protein |
| OZID_118 | F0743 | 29755 | 27902 | |
| OZID_118 | F0744 | 30586 | 30233 | |
| OZID_118 | F0745 | 31984 | 31295 | phage late gene regulator Q |
| OZID_118 | F0746 | 32340 | 31981 | putative endonuclease |
| OZID_118 | F0747 | 33402 | 32353 | |
| OZID_118 | F0748 | 33811 | 33404 | |
| OZID_118 | F0749 | 34398 | 34249 | |
| OZID_118 | F0750 | 35026 | 34463 | |
| OZID_118 | F0751 | 35446 | 35153 | |
| OZID_118 | F0752 | 35649 | 35461 | |
| OZID_118 | F0753 | 36002 | 35646 | |
| OZID_118 | F0754 | 36223 | 35999 | |
| OZID_118 | F0755 | 37009 | 36245 | |
| OZID_118 | F0756 | 37640 | 36978 | |
| OZID_118 | F0757 | 38475 | 37432 | |
| OZID_118 | F0758 | 38963 | 38538 | |
| OZID_118 | F0759 | 39187 | 38960 | putative regulator, cell division |
| OZID_118 | F0760 | 39282 | 39872 | |
| OZID_118 | F0761 | 40204 | 40356 | |
| OZID_118 | F0762 | 40837 | 41025 | putative inhibitor of cell division |
| OZID_118 | F0763 | 41022 | 41210 | |
| OZID_118 | F0764 | 41068 | 41166 | |
| OZID_118 | F0765 | 41306 | 43777 | |
| OZID_118 | F0766 | 43836 | 44039 | |
| OZID_118 | F0767 | 44039 | 45061 | integrase |
| OZID_12 | F0050 | 571 | 1749 | |
| OZID_12 | F0051 | 1951 | 2214 | |
| OZID_12 | F0052 | 2395 | 3567 | |
| OZID_120 | F0769 | 71 | 472 | |
| OZID_120 | F0770 | 469 | 816 | |
| OZID_121 | F0773 | 2019 | 2345 | unknown in IS |
| OZID_121 | F0774 | 2342 | 3232 | IS629 transposase |
| OZID_123 | F0777 | 845 | 180 | acetyl transferase; 0-antigen biosynthesis |
| OZID_123 | F0778 | 3478 | 2108 | phosphomannomutase |
| OZID_123 | F0779 | 4930 | 3482 | mannose-1-P guanosyltransferase |
| OZID_123 | F0780 | 5421 | 4912 | GDP-mannose mannosylhydrolase |
| OZID_123 | F0781 | 6395 | 5424 | fucose synthetase |
| OZID_123 | F0782 | 7510 | 6392 | GDP-mannose dehydratase |
| OZID_123 | F0783 | 8744 | 7530 | glycosyl transferase |
| OZID_123 | F0784 | 9869 | 8769 | perosamine synthetase |
| OZID_123 | F0785 | 11257 | 9866 | O antigen flippase |
| OZID_123 | F0786 | 11990 | 11244 | glycosyl transferase |
| OZID_123 | F0787 | 12942 | 11959 | O antigen polymerase |
| OZID_123 | F0788 | 13922 | 13140 | glycosyl transferase |
| OZID_124 | F0789 | 1232 | 237 | putative UDP-galactose 4-epimerase |
| OZID_126 | F0790 | 73 | 411 | |

TABLE 2-continued

| Sequence_ID | Orf_ID | Orf_Start | Orf_End | Description |
|---|---|---|---|---|
| OZID_126 | F0791 | 401 | 691 | putative regulator |
| OZID_128 | F0793 | 199 | 438 | |
| OZID_128 | F0794 | 1489 | 1836 | |
| OZID_128 | F0795 | 1846 | 2160 | |
| OZID_13 | F0054 | 1107 | 862 | early gene regulator |
| OZID_13 | F0055 | 1737 | 1348 | |
| OZID_13 | F0056 | 2458 | 1865 | repressor |
| OZID_13 | F0058 | 2679 | 2879 | antirepressor |
| OZID_13 | F0057 | 2783 | 2538 | |
| OZID_13 | F0059 | 2938 | 3291 | antiterminator |
| OZID_13 | F0060 | 3324 | 3932 | phage DNA replication |
| OZID_13 | F0061 | 3872 | 4246 | phage DNA replication |
| OZID_13 | F0062 | 4243 | 4554 | phage DNA replication |
| OZID_13 | F0063 | 4536 | 5264 | |
| OZID_13 | F0064 | 5276 | 5728 | phage tail protein |
| OZID_13 | F0065 | 6293 | 5700 | phage tail protein |
| OZID_13 | F0067 | 6781 | 7371 | DNA invertase |
| OZID_13 | F0066 | 6790 | 6293 | phage tail protein |
| OZID_13 | F0068 | 8202 | 7429 | |
| OZID_13 | F0070 | 9871 | 10089 | |
| OZID_13 | F0069 | 10176 | 9811 | |
| OZID_13 | F0071 | 10306 | 10458 | |
| OZID_134 | F0798 | 765 | 3656 | putative regulator |
| OZID_136 | F0800 | 167 | 370 | |
| OZID_136 | F0801 | 377 | 195 | |
| OZID_136 | F0802 | 560 | 408 | |
| OZID_139 | F0518 | 246 | 494 | |
| OZID_139 | F0517 | 1251 | 862 | |
| OZID_139 | F0822 | 3110 | 2511 | membrane protein |
| OZID_139 | F0825 | 6305 | 7339 | putative superoxide dismutase |
| OZID_139 | F0823 | 6678 | 3181 | phage tail protein |
| OZID_139 | F0826 | 8210 | 7530 | phage tail protein |
| OZID_139 | F0827 | 9085 | 8108 | phage tail protein |
| OZID_139 | F0828 | 9560 | 8862 | phage tail protein |
| OZID_139 | F0829 | 9901 | 9560 | phage tail protein |
| OZID_139 | F0830 | 12974 | 9894 | phage tail protein |
| OZID_139 | F0831 | 13308 | 13027 | |
| OZID_139 | F0832 | 13706 | 13332 | |
| OZID_139 | F0833 | 14557 | 13712 | |
| OZID_139 | F0835 | 14831 | 14487 | |
| OZID_139 | F0836 | 15274 | 14828 | |
| OZID_139 | F0837 | 15957 | 15631 | |
| OZID_139 | F0838 | 18538 | 16037 | |
| OZID_139 | F0839 | 18705 | 18484 | |
| OZID_139 | F0842 | 22412 | 20751 | |
| OZID_139 | F0843 | 22972 | 22409 | phage DNA packaging protein |
| OZID_139 | F0844 | 23545 | 23156 | |
| OZID_139 | F0845 | 24148 | 24513 | |
| OZID_139 | F0846 | 24726 | 24259 | cell lysis protein |
| OZID_139 | F0847 | 25449 | 24880 | |
| OZID_139 | F0848 | 26253 | 25720 | cell lysis protein |
| OZID_139 | F0849 | 26970 | 26551 | |
| OZID_139 | F0850 | 29100 | 27154 | |
| OZID_139 | F0851 | 29227 | 29550 | |
| OZID_139 | F0852 | 29880 | 29611 | shiga-like toxin 1 subunit B |
| OZID_139 | F0853 | 30837 | 29890 | shiga-like toxin 1 subunit A |
| OZID_139 | F0854 | 31817 | 31344 | phage late gene regulator Q |
| OZID_139 | F0855 | 32567 | 31962 | |
| OZID_139 | F0856 | 33172 | 32729 | |
| OZID_139 | F0857 | 33833 | 33306 | |
| OZID_139 | F0858 | 34375 | 33830 | |
| OZID_139 | F0859 | 34658 | 34233 | |
| OZID_139 | F0860 | 35106 | 34828 | |
| OZID_139 | F0861 | 35467 | 35177 | |
| OZID_139 | F0862 | 36165 | 35464 | |
| OZID_139 | F0863 | 37100 | 36162 | phage replication protein |
| OZID_139 | F0864 | 37429 | 37133 | phage regulatory protein |
| OZID_139 | F0865 | 37801 | 37544 | phage repressor |
| OZID_139 | F0866 | 37871 | 38518 | phage repressor |
| OZID_139 | F0867 | 38930 | 39481 | |
| OZID_139 | F0868 | 39964 | 40266 | |
| OZID_139 | F0869 | 40864 | 40403 | |
| OZID_139 | F0870 | 41125 | 41493 | ssDNA-binding protein |
| OZID_139 | F0871 | 41494 | 41730 | phage regulatory protein |
| OZID_139 | F0872 | 41918 | 42214 | recombination protein |

TABLE 2-continued

| Sequence_ID | Orf_ID | Orf_Start | Orf_End | Description |
|---|---|---|---|---|
| OZID_139 | F0873 | 42220 | 43005 | recombination protein |
| OZID_139 | F0874 | 43002 | 43679 | exonuclease |
| OZID_139 | F0875 | 44036 | 44317 | |
| OZID_139 | F0877 | 44634 | 45581 | |
| OZID_139 | F0878 | 45729 | 46016 | |
| OZID_139 | F0879 | 46093 | 46449 | |
| OZID_139 | F0880 | 46446 | 46808 | |
| OZID_139 | F0881 | 46896 | 47138 | |
| OZID_139 | F0882 | 47295 | 47549 | |
| OZID_139 | F0883 | 47583 | 48869 | putative integrase |
| OZID_14 | F0072 | 162 | 1007 | integrase |
| OZID_14 | F0073 | 1031 | 1342 | integrase |
| OZID_14 | F0074 | 1346 | 1762 | |
| OZID_14 | F0075 | 1735 | 2352 | |
| OZID_14 | F0076 | 2352 | 2810 | |
| OZID_14 | F0077 | 3045 | 3401 | |
| OZID_14 | F0078 | 3466 | 4056 | |
| OZID_14 | F0079 | 4056 | 4490 | |
| OZID_14 | F0080 | 5303 | 5031 | regulatory protein |
| OZID_14 | F0081 | 5860 | 5309 | |
| OZID_14 | F0082 | 6609 | 5857 | phage morphogenesis |
| OZID_14 | F0083 | 7543 | 7803 | DNA-binding protein; possible regulator |
| OZID_14 | F0084 | 7800 | 8357 | regulatory protein |
| OZID_14 | F0085 | 8354 | 8575 | |
| OZID_14 | F0086 | 8575 | 8898 | |
| OZID_14 | F0087 | 8912 | 11245 | replication protein (primase) |
| OZID_14 | F0088 | 12334 | 11378 | |
| OZID_141 | F0884 | 342 | 13 | |
| OZID_142 | F0885 | 1312 | 119 | putative hydroxylase |
| OZID_142 | F0886 | 1881 | 1327 | putative glutathione-S-transferase |
| OZID_142 | F0887 | 2681 | 1980 | putative isomerase-decarboxylase |
| OZID_142 | F0888 | 3724 | 2696 | putative 1,2-dioxygenase |
| OZID_142 | F0889 | 4830 | 3736 | putative transporter |
| OZID_142 | F0890 | 5173 | 6129 | putative regulator |
| OZID_145 | F0895 | 455 | 1525 | |
| OZID_149 | F0901 | 1012 | 170 | |
| OZID_149 | F0902 | 1562 | 1014 | putative minor fimbrial subunit |
| OZID_149 | F0903 | 2002 | 1532 | putative minor fimbrial subunit |
| OZID_149 | F0904 | 2601 | 1999 | putative minor fimbrial subunit |
| OZID_149 | F0905 | 3268 | 2510 | putative fimbrial chaperone |
| OZID_149 | F0908 | 5942 | 3291 | putative fimbrial usher |
| OZID_149 | F0909 | 6575 | 6012 | putative major fimbrial subunit |
| OZID_15 | F0090 | 645 | 1382 | putative oxidoreductase |
| OZID_15 | F0091 | 1549 | 1827 | |
| OZID_15 | F0092 | 3432 | 2530 | putative LysR-like transcriptional regulator |
| OZID_15 | F0093 | 3579 | 4736 | |
| OZID_15 | F0095 | 4812 | 6005 | |
| OZID_150 | F1490 | 1541 | 408 | |
| OZID_151 | F0911 | 1312 | 176 | |
| OZID_151 | F0913 | 2002 | 1322 | |
| OZID_151 | F0914 | 2459 | 1989 | |
| OZID_151 | F0916 | 3008 | 3703 | |
| OZID_151 | F0915 | 3025 | 2456 | |
| OZID_151 | F0917 | 3880 | 3635 | |
| OZID_151 | F0918 | 5785 | 4373 | |
| OZID_151 | F0919 | 6148 | 5972 | |
| OZID_151 | F0920 | 6451 | 7077 | putative resolvase |
| OZID_151 | F0921 | 8922 | 7675 | sucrose permease |
| OZID_151 | F0922 | 9908 | 8994 | D-fructokinase |
| OZID_151 | F0923 | 10115 | 11557 | sucrose hydrolase |
| OZID_151 | F0924 | 12653 | 11565 | sucrose specific transcriptional regulator |
| OZID_152 | F0926 | 1251 | 43 | |
| OZID_156 | F0931 | 862 | 8 | |
| OZID_156 | F0932 | 1683 | 862 | putative DMSO reductase subunit C |
| OZID_156 | F0933 | 2305 | 1676 | putative DMSO reductase subunit B |
| OZID_156 | F0934 | 4683 | 2302 | putative DMSO reductase subunit A |
| OZID_159 | F0937 | 98 | 289 | |
| OZID_159 | F0938 | 268 | 516 | |

TABLE 2-continued

| Sequence_ID | Orf_ID | Orf_Start | Orf_End | Description |
|---|---|---|---|---|
| OZID_159 | F0939 | 670 | 840 | |
| OZID_159 | F0940 | 1608 | 1018 | putative chaperone |
| OZID_159 | F0941 | 1791 | 2441 | |
| OZID_159 | F0942 | 2520 | 3578 | |
| OZID_16 | F0096 | 72 | 473 | |
| OZID_16 | F0097 | 470 | 817 | |
| OZID_16 | F0098 | 867 | 2405 | |
| OZID_160 | F1390 | 507 | 277 | |
| OZID_160 | F1391 | 905 | 558 | |
| OZID_160 | F1345 | 1227 | 907 | |
| OZID_160 | F1346 | 3125 | 1272 | |
| OZID_160 | F1347 | 3366 | 3695 | |
| OZID_160 | F0956 | 4544 | 3786 | |
| OZID_160 | F0957 | 5405 | 4782 | phage late gene regulator Q |
| OZID_160 | F0958 | 6067 | 5402 | |
| OZID_160 | F0959 | 6705 | 6064 | |
| OZID_160 | F0960 | 7297 | 6650 | |
| OZID_160 | F0961 | 7552 | 8307 | transposase for IS30 |
| OZID_160 | F0962 | 8367 | 8645 | |
| OZID_160 | F0963 | 9092 | 8721 | |
| OZID_160 | F0964 | 9942 | 9004 | |
| OZID_160 | F0965 | 10808 | 10338 | |
| OZID_160 | F0966 | 11247 | 10849 | |
| OZID_160 | F0967 | 11838 | 11248 | |
| OZID_160 | F0968 | 12878 | 11871 | |
| OZID_160 | F0969 | 13366 | 12875 | integrase |
| OZID_160 | F0970 | 15403 | 14465 | integrase |
| OZID_160 | F0971 | 15926 | 15720 | phage regulatory protein |
| OZID_160 | F0972 | 16877 | 16026 | |
| OZID_161 | F0973 | 1469 | 135 | putative regulator |
| OZID_161 | F0974 | 1557 | 1988 | |
| OZID_163 | F0976 | 277 | 41 | |
| OZID_163 | F0977 | 1715 | 288 | |
| OZID_163 | F0978 | 2308 | 1715 | putative decarboxylase |
| OZID_163 | F0979 | 2422 | 2862 | putative regulator |
| OZID_164 | F0981 | 572 | 279 | |
| OZID_164 | F0982 | 669 | 472 | |
| OZID_164 | F0983 | 1492 | 569 | |
| OZID_164 | F0984 | 2271 | 1489 | |
| OZID_164 | F0985 | 2867 | 2121 | |
| OZID_164 | F0986 | 3933 | 2878 | |
| OZID_164 | F0987 | 4481 | 3945 | |
| OZID_164 | F0988 | 6040 | 4478 | |
| OZID_164 | F0989 | 8837 | 6138 | |
| OZID_166 | F0991 | 268 | 567 | |
| OZID_166 | F0992 | 551 | 1255 | |
| OZID_166 | F0993 | 1489 | 2637 | |
| OZID_168 | F0998 | 932 | 198 | putative lipoprotein |
| OZID_168 | F0999 | 1261 | 929 | putative Type III secretion apparatus protein |
| OZID_168 | F1000 | 2979 | 3479 | putative response regulator of two component tranport system |
| OZID_168 | F1001 | 4957 | 3836 | putative integral membrane protein-component of type III secretion apparatus |
| OZID_168 | F1002 | 5202 | 4966 | putative integral membrane protein-component of type III secretion apparatus |
| OZID_168 | F1003 | 5733 | 5281 | putative integral membrane protein-component of type III secretion apparatus |
| OZID_168 | F1004 | 6671 | 6006 | putative integral membrane protein-component of type III secretion apparatus |
| OZID_168 | F1005 | 7692 | 6661 | type III secretion apparatus protein |
| OZID_168 | F1006 | 8176 | 7607 | type III secretion apparatus protein |
| OZID_168 | F1007 | 8482 | 8249 | |
| OZID_168 | F1009 | 10227 | 8908 | type III secretion apparatus protein |
| OZID_168 | F1010 | 12292 | 10232 | type III secretion apparatus protein |
| OZID_168 | F1012 | 13454 | 12285 | secreted protein |
| OZID_168 | F1013 | 15138 | 13435 | putative InvG-like protein |
| OZID_168 | F1014 | 15884 | 15135 | putative InvF-like protein |

TABLE 2-continued

| Sequence_ID | Orf_ID | Orf_Start | Orf_End | Description |
|---|---|---|---|---|
| OZID_168 | F1015 | 16409 | 16230 | |
| OZID_17 | F0100 | 2207 | 1287 | |
| OZID_17 | F0101 | 2301 | 3290 | putative LysR-like transcriptional regulator |
| OZID_17 | F0102 | 3934 | 3578 | |
| OZID_17 | F0104 | 4702 | 4127 | |
| OZID_172 | F1019 | 150 | 581 | |
| OZID_172 | F1020 | 604 | 1182 | |
| OZID_172 | F1021 | 1183 | 1890 | |
| OZID_172 | F1022 | 1872 | 2555 | putative ATP-binding protein of ABC transport system |
| OZID_172 | F1023 | 2516 | 3226 | putative ATP-binding protein of ABC transport system |
| OZID_173 | F1025 | 789 | 58 | |
| OZID_175 | F1027 | 197 | 1462 | putative P4 integrase |
| OZID_175 | F1028 | 2364 | 1579 | |
| OZID_175 | F1029 | 2396 | 3127 | |
| OZID_175 | F1030 | 3124 | 3471 | |
| OZID_175 | F1031 | 3491 | 4939 | |
| OZID_175 | F1032 | 5696 | 4740 | |
| OZID_175 | F1033 | 6341 | 5793 | putative PagC-like membrane protein |
| OZID_175 | F1034 | 7114 | 6914 | |
| OZID_175 | F1035 | 7643 | 8533 | putative transposase |
| OZID_175 | F1036 | 8886 | 9113 | |
| OZID_175 | F1037 | 9321 | 10970 | putative enterotoxin |
| OZID_175 | F1038 | 11578 | 12567 | |
| OZID_175 | F1039 | 12832 | 13290 | |
| OZID_175 | F1040 | 13668 | 14513 | |
| OZID_175 | F1041 | 15165 | 16466 | putative cytotoxin |
| OZID_175 | F1042 | 16751 | 17299 | putative cytotoxin |
| OZID_175 | F1043 | 18229 | 17339 | putative transposase |
| OZID_175 | F1044 | 18552 | 18226 | orf; hypothetical protein in IS |
| OZID_175 | F1045 | 18743 | 19090 | |
| OZID_175 | F1046 | 19140 | 20678 | |
| OZID_175 | F1050 | 20746 | 20904 | |
| OZID_175 | F1051 | 20901 | 21251 | |
| OZID_175 | F1052 | 21734 | 22864 | |
| OZID_175 | F1053 | 22914 | 23126 | putative transposase for IS3, partial |
| OZID_176 | F1054 | 931 | 44 | |
| OZID_176 | F1055 | 1935 | 928 | putative iron compound-binding protein of ABC transporter family |
| OZID_176 | F1056 | 2935 | 1886 | putative iron compound permease protein of ABC transporter family |
| OZID_176 | F1057 | 3915 | 2932 | putative iron compound permease protein of ABC transporter family |
| OZID_176 | F1058 | 4721 | 3912 | putative ATP-binding protein of ABC transporter family |
| OZID_176 | F1059 | 5095 | 7236 | putative iron compound receptor |
| OZID_178 | F1061 | 356 | 159 | |
| OZID_181 | F1064 | 393 | 1271 | putative phosphotransferase system enzyme subunit |
| OZID_181 | F1065 | 1289 | 1723 | putative phosphotransferase system enzyme subunit |
| OZID_182 | F1068 | 54 | 380 | orf; hypothetical protein in IS |
| OZID_182 | F1069 | 377 | 1267 | putative IS629 transposase |
| OZID_185 | F1072 | 194 | 661 | putative leader peptidase |
| OZID_187 | F1076 | 56 | 340 | |
| OZID_187 | F1077 | 331 | 816 | |
| OZID_188 | F1080 | 1529 | 537 | |
| OZID_189 | F1082 | 1340 | 45 | |
| OZID_189 | F1084 | 1471 | 1247 | ATP-dependent DNA helicase (together with next 3 orfs) |
| OZID_189 | F1085 | 2373 | 1399 | ATP-dependent DNA helicase (together with adjacent 3 orfs) |
| OZID_189 | F1086 | 2766 | 2377 | ATP-dependent DNA helicase (together with adjacent 3 orfs) |
| OZID_189 | F1087 | 3371 | 2763 | ATP-dependent DNA helicase (together with adjacent 3 orfs) |
| OZID_190 | F1088 | 210 | 1121 | |
| OZID_190 | F1089 | 1486 | 1070 | |
| OZID_191 | F1091 | 179 | 27 | |
| OZID_191 | F1092 | 922 | 176 | |
| OZID_192 | F1094 | 793 | 527 | |

TABLE 2-continued

| Sequence_ID | Orf_ID | Orf_Start | Orf_End | Description |
|---|---|---|---|---|
| OZID_193 | F1096 | 383 | 772 | |
| OZID_193 | F1097 | 832 | 1899 | |
| OZID_193 | F1098 | 1940 | 2662 | |
| OZID_193 | F1099 | 2641 | 3480 | |
| OZID_193 | F1100 | 3455 | 3712 | putative acyl carrier protein |
| OZID_193 | F1101 | 3724 | 3975 | putative acyl carrier protein |
| OZID_193 | F1102 | 3980 | 4561 | |
| OZID_193 | F1103 | 4519 | 5919 | putative enzyme |
| OZID_193 | F1104 | 5876 | 6259 | putative enzyme |
| OZID_193 | F1105 | 6250 | 7926 | putative enzyme |
| OZID_193 | F1106 | 7930 | 8352 | |
| OZID_193 | F1107 | 8349 | 8954 | |
| OZID_193 | F1108 | 8923 | 11241 | |
| OZID_193 | F1109 | 11238 | 11822 | |
| OZID_193 | F1110 | 11824 | 12993 | putative 3-oxoacyl-[ACP] synthase |
| OZID_193 | F1111 | 12990 | 13454 | |
| OZID_193 | F1112 | 13454 | 14185 | putative beta-ketoacyl-ACP reductase |
| OZID_194 | F1115 | 191 | 946 | putative regulator |
| OZID_194 | F1116 | 971 | 1444 | putative phosphotransferase system enzyme subunit |
| OZID_194 | F1117 | 1441 | 1722 | putative phosphotransferase system enzyme subunit |
| OZID_194 | F1118 | 1769 | 3157 | putative phosphotransferase system enzyme subunit |
| OZID_194 | F1119 | 3150 | 4658 | putative xylulose kinase |
| OZID_194 | F1120 | 4648 | 4917 | putative phosphocarrier protein |
| OZID_194 | F1121 | 4949 | 5809 | putative aldolase |
| OZID_194 | F1122 | 6218 | 5859 | |
| OZID_194 | F1123 | 6490 | 6215 | |
| OZID_196 | F1124 | 1087 | 59 | putative heme/hemoglobin transport protein |
| OZID_196 | F1125 | 3118 | 1136 | outer membrane heme/hemoglobin receptor |
| OZID_196 | F1127 | 3801 | 4715 | putative periplasmic binding protein |
| OZID_196 | F1128 | 4735 | 6072 | putative oxygen independent coproporphyrinogen III oxidase |
| OZID_196 | F1129 | 6085 | 6579 | |
| OZID_196 | F1130 | 6579 | 7202 | |
| OZID_196 | F1131 | 7251 | 8243 | putative permease of iron compound ABC transport system |
| OZID_196 | F1132 | 8210 | 9010 | putative ATP-binding component of iron compound transport system |
| OZID_197 | F1133 | 601 | 71 | putative fimbrial subunit |
| OZID_197 | F1134 | 1661 | 606 | putative fimbrial protein |
| OZID_197 | F1135 | 3133 | 1676 | putative fimbrial usher |
| OZID_197 | F1136 | 4249 | 3146 | putative fimbrial usher |
| OZID_197 | F1138 | 4976 | 4278 | putative fimbrial chaperone |
| OZID_197 | F1139 | 5565 | 5029 | putative major fimbrial subunit |
| OZID_199 | F1141 | 937 | 2337 | putative permease |
| OZID_202 | F1146 | 868 | 1224 | |
| OZID_202 | F1147 | 1268 | 6034 | putative adhesin |
| OZID_203 | F1148 | 87 | 1295 | putative LPS biosynthesis enzyme |
| OZID_203 | F1149 | 2473 | 1331 | putative LPS biosynthesis enzyme |
| OZID_203 | F1150 | 3036 | 2482 | putative LPS biosynthesis enzyme |
| OZID_203 | F1151 | 4227 | 3520 | putative LPS biosynthesis enzyme |
| OZID_203 | F1152 | 5260 | 4253 | putative LPS biosynthesis enzyme |
| OZID_208 | L0003 | 181 | 1362 | putative P4-family integrase |
| OZID_208 | L0004 | 1461 | 1811 | unknown in IS |
| OZID_208 | L0005 | 1824 | 2006 | |
| OZID_208 | L0006 | 2024 | 2677 | unknown in IS |
| OZID_208 | L0007 | 2928 | 3302 | |
| OZID_208 | L0008 | 3299 | 3790 | |
| OZID_208 | L0009 | 3802 | 3999 | |
| OZID_208 | L0010 | 4084 | 4425 | |
| OZID_208 | L0012 | 4626 | 4811 | |
| OZID_208 | L0011 | 4652 | 4422 | |
| OZID_208 | L0013 | 5181 | 5582 | unknown in ISEc8 |

TABLE 2-continued

| Sequence_ID | Orf_ID | Orf_Start | Orf_End | Description |
|---|---|---|---|---|
| OZID_208 | L0014 | 5579 | 5926 | unknown in ISEc8 |
| OZID_208 | L0015 | 5976 | 7514 | unknown in ISEc8 |
| OZID_208 | L0016 | 9125 | 8379 | putative secreted protein |
| OZID_208 | L0017 | 9488 | 9210 | |
| OZID_208 | L0018 | 9715 | 9494 | type III secretion apparatus protein |
| OZID_208 | L0019 | 10158 | 9751 | |
| OZID_208 | L0020 | 11103 | 10165 | secreted protein |
| OZID_208 | L0021 | 12248 | 11124 | secreted protein |
| OZID_208 | L0022 | 12839 | 12261 | secreted protein |
| OZID_208 | L0023 | 13953 | 12898 | putative type III secretion apparatus protein |
| OZID_208 | L0024 | 14096 | 15316 | type III secretion apparatus protein |
| OZID_208 | L0025 | 18384 | 15580 | intimin protein |
| OZID_208 | L0026 | 18914 | 18444 | putative chaperone |
| OZID_208 | L0027 | 20728 | 19052 | translocated intimin receptor |
| OZID_208 | L0028 | 21763 | 21152 | |
| OZID_208 | L0029 | 22029 | 22412 | |
| OZID_208 | L0030 | 23116 | 22610 | |
| OZID_208 | L0031 | 24064 | 23147 | putative type III secretion apparatus protein |
| OZID_208 | L0032 | 24302 | 24027 | |
| OZID_208 | L0033 | 24813 | 24436 | |
| OZID_208 | L0034 | 26156 | 24816 | type III secretion apparatus protein |
| OZID_208 | L0035 | 28167 | 26140 | type III secretion apparatus protein |
| OZID_208 | L0036 | 28517 | 28164 | |
| OZID_208 | L0037 | 28702 | 29001 | putative type III secretion apparatus protein |
| OZID_208 | L0038 | 29034 | 29462 | |
| OZID_208 | L0039 | 29465 | 30037 | type III secretion apparatus protein |
| OZID_208 | L0040 | 30043 | 30498 | |
| OZID_208 | L0041 | 30498 | 32036 | type III secretion apparatus protein |
| OZID_208 | L0042 | 32050 | 32505 | chaperone of espD |
| OZID_208 | L0043 | 33302 | 32889 | |
| OZID_208 | L0044 | 33728 | 33357 | |
| OZID_208 | L0045 | 33924 | 34382 | |
| OZID_208 | L0046 | 35416 | 34379 | type III secretion apparatus protein |
| OZID_208 | L0047 | 36185 | 35409 | type III secretion apparatus protein |
| OZID_208 | L0048 | 36454 | 36185 | type III secretion apparatus protein |
| OZID_208 | L0049 | 37107 | 36454 | type III secretion apparatus protein |
| OZID_208 | L0050 | 37807 | 37112 | |
| OZID_208 | L0051 | 38351 | 37752 | |
| OZID_208 | L0052 | 38671 | 38348 | |
| OZID_208 | L0053 | 38893 | 38675 | |
| OZID_208 | L0054 | 39297 | 38908 | |
| OZID_208 | L0055 | 40542 | 41738 | |
| OZID_208 | L0056 | 41866 | 42684 | |
| OZID_209 | F1212 | 139 | 492 | |
| OZID_209 | F1213 | 476 | 799 | |
| OZID_21 | F0108 | 322 | 74 | |
| OZID_21 | F0109 | 1349 | 240 | |
| OZID_21 | F0110 | 2137 | 1376 | |
| OZID_21 | F0112 | 2875 | 2291 | |
| OZID_21 | F0114 | 3122 | 2967 | |
| OZID_21 | F0116 | 3573 | 3415 | |
| OZID_21 | F0117 | 3977 | 3594 | |
| OZID_21 | F0118 | 4400 | 4242 | |
| OZID_210 | F1215 | 1203 | 100 | |
| OZID_210 | F1216 | 1596 | 1219 | |
| OZID_210 | F1217 | 2293 | 1811 | |
| OZID_210 | F1218 | 3106 | 2441 | |
| OZID_212 | F1222 | 377 | 147 | |
| OZID_212 | F1223 | 2331 | 328 | |
| OZID_214 | F1224 | 2545 | 137 | |
| OZID_214 | F1227 | 6763 | 4502 | |
| OZID_214 | F1229 | 7083 | 7268 | |
| OZID_214 | F1228 | 7174 | 6968 | |

TABLE 2-continued

| Sequence_ID | Orf_ID | Orf_Start | Orf_End | Description |
|---|---|---|---|---|
| OZID_215 | F1231 | 1188 | 106 | putative fimbrial protein |
| OZID_215 | F1232 | 2286 | 1216 | putative fimbrial protein |
| OZID_215 | F1233 | 4832 | 2298 | putative fimbrial usher |
| OZID_215 | F1234 | 5015 | 4854 | putative fimbrial chaperone |
| OZID_215 | F1236 | 5539 | 5156 | putative fimbrial chaperone |
| OZID_215 | F1237 | 6245 | 5643 | putative major fimbrial subuit |
| OZID_216 | F1239 | 920 | 18 | orf; conserved hypothetical protein |
| OZID_217 | F1240 | 532 | 41 | |
| OZID_217 | F1241 | 1377 | 529 | |
| OZID_217 | F1242 | 2121 | 1735 | |
| OZID_217 | F1243 | 2326 | 2637 | |
| OZID_22 | F0120 | 468 | 4517 | putative beta-barrel outer membrane protein |
| OZID_222 | F1245 | 918 | 43 | |
| OZID_224 | F1249 | 835 | 1749 | |
| OZID_224 | F1250 | 1857 | 1675 | |
| OZID_225 | F1252 | 317 | 1711 | putative glycoporin |
| OZID_227 | F1255 | 753 | 37 | |
| OZID_227 | F1256 | 1472 | 786 | |
| OZID_228 | F1257 | 105 | 4289 | Rhs core protein |
| OZID_228 | F1258 | 4580 | 4858 | |
| OZID_228 | F1259 | 4897 | 4583 | orf; hypothetical protein in IS |
| OZID_228 | F1260 | 5076 | 4891 | orf; hypothetical protein in IS |
| OZID_228 | F1261 | 5375 | 5103 | putative transposase |
| OZID_229 | F1262 | 200 | 1366 | putative hippuricase |
| OZID_232 | F1266 | 1533 | 292 | putative L-sorbose-1-P-reductase |
| OZID_232 | F1267 | 2397 | 1573 | putative sorbose PTS component |
| OZID_232 | F1268 | 3205 | 2408 | putative sorbose PTS component |
| OZID_232 | F1269 | 3765 | 3271 | putative sorbose PTS component |
| OZID_232 | F1270 | 4172 | 3765 | putative sorbose PTS component |
| OZID_232 | F1271 | 4988 | 4182 | putative D-glucitol-6-P-dehydrogenase |
| OZID_232 | F1272 | 6050 | 5058 | putative transcriptional regulator of sorbose uptake and utilizatio genes |
| OZID_233 | F1274 | 51 | 776 | putative response regulator |
| OZID_233 | F1275 | 1774 | 773 | |
| OZID_233 | F1276 | 2631 | 1771 | putative aldolase |
| OZID_233 | F1277 | 3329 | 2646 | |
| OZID_233 | F1278 | 4325 | 3384 | putative ribose binding protein of ABC transport system |
| OZID_233 | F1279 | 5318 | 4344 | putative permease of ribose ABC transport system |
| OZID_233 | F1281 | 6772 | 9045 | putative histidine kinase |
| OZID_233 | F1280 | 6868 | 5315 | putative ATP-binding protein of ribose ABC transport system |
| OZID_233 | F1282 | 9042 | 9218 | |
| OZID_235 | F1285 | 487 | 56 | putative transposase |
| OZID_235 | F1286 | 495 | 1703 | |
| OZID_242 | F1291 | 89 | 2038 | putative transposase or integrase |
| OZID_242 | F1487 | 2238 | 2564 | |
| OZID_242 | F1293 | 2561 | 3451 | IS629 transposase |
| OZID_242 | F1294 | 4011 | 3634 | |
| OZID_242 | F1295 | 4399 | 4133 | |
| OZID_242 | F1296 | 5936 | 5469 | |
| OZID_242 | F1297 | 6123 | 6698 | putative resolvase |
| OZID_242 | F1298 | 8213 | 6897 | |
| OZID_242 | F1299 | 9138 | 8365 | |
| OZID_242 | F1300 | 9255 | 9719 | |
| OZID_243 | F1302 | 105 | 272 | putative transposase |
| OZID_244 | F1304 | 1663 | 560 | |
| OZID_244 | F1305 | 2374 | 1667 | |
| OZID_244 | F1307 | 4090 | 2381 | |
| OZID_244 | F1308 | 4251 | 7604 | |
| OZID_244 | F1310 | 7595 | 13918 | |
| OZID_244 | F1311 | 14142 | 17000 | putative ATP-dependent helicase |

TABLE 2-continued

| Sequence_ID | Orf_ID | Orf_Start | Orf_End | Description |
|---|---|---|---|---|
| OZID_244 | F1312 | 17003 | 21937 | |
| OZID_244 | F1313 | 21937 | 28278 | putative helicase |
| OZID_244 | F1314 | 28275 | 30389 | putative helicase |
| OZID_244 | F1315 | 31336 | 31154 | |
| OZID_244 | F1316 | 31587 | 31342 | |
| OZID_244 | F1317 | 31829 | 31518 | |
| OZID_245 | F1318 | 5257 | 155 | putative invasin |
| OZID_246 | F1320 | 2459 | 264 | |
| OZID_248 | F1322 | 92 | 973 | orf; conserved hypothetical protein |
| OZID_248 | F1323 | 1021 | 2184 | orf; conserved hypothetical protein |
| OZID_249 | F1325 | 1843 | 89 | putative restriction modification enzyme S subunit |
| OZID_249 | F1326 | 3348 | 1843 | putative restriction modification enzyme M subunit (methylase) |
| OZID_249 | F1327 | 5811 | 3379 | putative restriction modification enzyme R subunit (endonucleas |
| OZID_249 | F1328 | 6089 | 6373 | orf; conserved hypothetical protein |
| OZID_249 | F1329 | 6643 | 7740 | orf; conserved hypothetical protein |
| OZID_250 | F1330 | 651 | 109 | |
| OZID_253 | F1468 | 1291 | 692 | membrane protein |
| OZID_253 | F1467 | 4126 | 1358 | phage tail protein |
| OZID_253 | F1466 | 4755 | 4060 | phage tail protein |
| OZID_253 | F1465 | 5487 | 4816 | phage tail protein |
| OZID_253 | F1464 | 6128 | 5385 | phage tail protein |
| OZID_253 | F1463 | 6832 | 6134 | phage tail protein |
| OZID_253 | F1462 | 7161 | 6832 | phage tail protein |
| OZID_253 | F1461 | 9707 | 7158 | phage tail protein |
| OZID_253 | F1460 | 10134 | 9700 | phage tail protein |
| OZID_253 | F1459 | 10538 | 10116 | phage tail protein |
| OZID_253 | F1458 | 11324 | 10554 | phage tail protein |
| OZID_253 | F1457 | 11484 | 11302 | phage tail protein |
| OZID_253 | F1456 | 11675 | 11433 | phage tail protein |
| OZID_253 | F1454 | 12269 | 11691 | phage tail protein |
| OZID_253 | F1453 | 12634 | 12281 | phage morphogenesis protein |
| OZID_253 | F1450 | 14505 | 14167 | phage morphogenesis protein |
| OZID_253 | F1449 | 15057 | 14509 | phage capsid protein |
| OZID_253 | F1448 | 15791 | 14901 | phage capsid protein |
| OZID_253 | F1447 | 17412 | 15811 | phage capsid protein |
| OZID_253 | F1446 | 17615 | 17409 | phage morphogenesis protein |
| OZID_253 | F1444 | 19537 | 17612 | phage DNA packaging protein |
| OZID_253 | F1443 | 20057 | 19512 | phage DNA packaging protein |
| OZID_253 | F1441 | 21837 | 21529 | cell lysis protein |
| OZID_254 | F1362 | 2117 | 1836 | |
| OZID_254 | F1361 | 2515 | 2141 | |
| OZID_254 | F1360 | 3309 | 2521 | |
| OZID_254 | F1359 | 3650 | 3306 | |
| OZID_254 | F1358 | 4093 | 3647 | |
| OZID_254 | F1357 | 4440 | 4090 | |
| OZID_254 | F1356 | 4776 | 4450 | |
| OZID_254 | F1355 | 5834 | 4773 | |
| OZID_254 | F1354 | 7195 | 5831 | |
| OZID_254 | F1351 | 11059 | 9461 | |
| OZID_254 | F0948 | 12283 | 11918 | |
| OZID_255 | F1366 | 2147 | 1467 | |
| OZID_255 | F1365 | 2959 | 2045 | |
| OZID_255 | F1363 | 3838 | 3497 | |
| OZID_256 | F1421 | 718 | 1593 | putative lambdoid phage tail fiber component |
| OZID_256 | F1422 | 1590 | 1886 | putative lambdoid phage tail fiber component |
| OZID_256 | F1423 | 1981 | 2346 | putative lambdoid phage tail fiber component, partial |
| OZID_256 | 1424 | 2356 | 2619 | putative lambdoid phage tail fiber component, partial |
| OZID_256 | F1427 | 3271 | 3780 | putative lambdoid phage tail fiber component, partial |
| OZID_256 | F1428 | 3659 | 3949 | putative lambdoid phage tail fiber component, partial |
| OZID_256 | F1429 | 4190 | 5365 | putative lambdoid phage tail fiber component, partial |
| OZID_256 | F1430 | 5242 | 5991 | putative lambdoid phage tail fiber component, partial |
| OZID_256 | F1431 | 5840 | 7450 | putative lambdoid phage tail fiber component, partial |

TABLE 2-continued

| Sequence_ID | Orf_ID | Orf_Start | Orf_End | Description |
|---|---|---|---|---|
| OZID_256 | F1432 | 7453 | 7668 | putative lambdoid phage tail fiber component, partial |
| OZID_256 | F1433 | 7736 | 8335 | membrane protein |
| OZID_257 | F1437 | 1353 | 1057 | |
| OZID_26 | F0125 | 229 | 1215 | putative periplasmic binding protein, probable substrate ribose |
| OZID_26 | F0126 | 1264 | 1524 | putative ATP-binding component of transport system |
| OZID_26 | F0127 | 1570 | 2748 | putative ATP-binding component of transport system, probably ribose specific |
| OZID_26 | F0128 | 2741 | 3712 | putative permease component of transport system, probably ribose specific |
| OZID_28 | F0131 | 1728 | 940 | |
| OZID_29 | F0132 | 1116 | 58 | putative ATP-binding component of transport system for ferric iro |
| OZID_29 | F0133 | 3194 | 1116 | putative permease component of transport system for ferric iron |
| OZID_29 | F0134 | 4294 | 3263 | periplasmic ferric iron-binding protein |
| OZID_29 | F0135 | 5607 | 4291 | putative permease; hexosephosphate transport |
| OZID_29 | F0136 | 7221 | 5680 | putative sensor kinase; hexosephosphate transport |
| OZID_29 | F0137 | 7850 | 7221 | putative response regulator; hexosephosphate transport |
| OZID_3 | F0009 | 77 | 310 | putative antitoxin of gyrase inhibiting toxin-antitoxin system |
| OZID_3 | F0008 | 171 | 1 | |
| OZID_3 | F0010 | 313 | 627 | putative toxin of gyrase inhibiting toxin-antitoxin system |
| OZID_34 | F0141 | 70 | 237 | |
| OZID_34 | F0142 | 188 | 1633 | |
| OZID_35 | F0143 | 150 | 392 | |
| OZID_35 | F0144 | 352 | 666 | |
| OZID_36 | F0145 | 1753 | 182 | |
| OZID_39 | F0146 | 310 | 1665 | putative outer membrane export protein for RTX-like exoprotein |
| OZID_39 | F0147 | 1768 | 6153 | |
| OZID_39 | F0148 | 6361 | 21927 | |
| OZID_39 | F0149 | 21931 | 24093 | putative cytoplasmic membrane export protein for RTX-like exoprotein |
| OZID_40 | F0011 | 207 | 776 | |
| OZID_40 | F0151 | 207 | 4 | |
| OZID_40 | F0152 | 626 | 204 | |
| OZID_40 | F0153 | 1727 | 711 | |
| OZID_40 | F0154 | 2094 | 2456 | |
| OZID_43 | F0156 | 1260 | 124 | |
| OZID_43 | F0157 | 3057 | 1723 | |
| OZID_43 | F0158 | 8588 | 3651 | |
| OZID_43 | F0159 | 9069 | 8608 | |
| OZID_43 | F0160 | 10998 | 9097 | |
| OZID_44 | F0161 | 230 | 481 | |
| OZID_47 | F0162 | 232 | 432 | |
| OZID_47 | F0163 | 544 | 374 | |
| OZID_47 | F0164 | 917 | 702 | |
| OZID_47 | F0165 | 1136 | 1288 | |
| OZID_49 | F0167 | 564 | 1469 | putative LysR-like transcriptional regulator |
| OZID_49 | F0168 | 2105 | 1503 | putative corrinoid: ATP adenosyltransferase |
| OZID_49 | F0169 | 3767 | 2115 | putative fumarate hydratase |
| OZID_49 | F0170 | 4450 | 3875 | |
| OZID_49 | F0171 | 5175 | 4393 | |
| OZID_49 | F0172 | 5632 | 5315 | |
| OZID_49 | F0173 | 6999 | 5629 | |
| OZID_49 | F0174 | 8244 | 7003 | putative methylaspartate ammonia-lyase |
| OZID_49 | F0175 | 11096 | 9708 | putative glutamate mutase |

TABLE 2-continued

| Sequence_ID | Orf_ID | Orf_Start | Orf_End | Description |
|---|---|---|---|---|
| OZID_49 | F0176 | 11608 | 11096 | putative methylaspartate mutase |
| OZID_49 | F0177 | 11899 | 11732 | |
| OZID_49 | F0178 | 12515 | 12093 | |
| OZID_49 | F0179 | 13541 | 12597 | |
| OZID_52 | F0180 | 855 | 85 | integrase |
| OZID_52 | F0181 | 1825 | 2400 | |
| OZID_52 | F0183 | 3159 | 3344 | |
| OZID_52 | F0182 | 3212 | 2931 | |
| OZID_52 | F0184 | 4246 | 3566 | exonuclease |
| OZID_52 | F0185 | 4803 | 4243 | |
| OZID_52 | F0186 | 5283 | 5906 | |
| OZID_52 | F0187 | 6134 | 6565 | |
| OZID_52 | F0188 | 7736 | 6777 | |
| OZID_52 | F0189 | 8127 | 8900 | phage late gene regulator Q |
| OZID_52 | F0190 | 9069 | 9827 | |
| OZID_52 | F0191 | 10648 | 10908 | cell lysis protein |
| OZID_52 | F0192 | 10908 | 11405 | cell lysis protein |
| OZID_52 | F0193 | 11402 | 11869 | cell lysis protein |
| OZID_52 | F0194 | 11866 | 12009 | |
| OZID_52 | F0195 | 12305 | 12694 | |
| OZID_52 | F0196 | 12684 | 13175 | |
| OZID_52 | F0197 | 13175 | 15277 | DNA packaging protein |
| OZID_52 | F0198 | 15274 | 15486 | |
| OZID_52 | F0199 | 15414 | 16019 | |
| OZID_52 | F0200 | 16016 | 16537 | |
| OZID_52 | F0201 | 16789 | 18966 | peptidase |
| OZID_52 | F0202 | 19053 | 19376 | |
| OZID_52 | F0203 | 19369 | 19644 | |
| OZID_52 | F0204 | 19656 | 20234 | phage morphogenesis protein |
| OZID_52 | F0205 | 20231 | 20632 | phage morphogenesis protein |
| OZID_52 | F0206 | 20568 | 21386 | phage morphogenesis protein |
| OZID_52 | F0207 | 21435 | 21833 | phage morphogenesis protein |
| OZID_52 | F0208 | 21842 | 22171 | phage morphogenesis protein |
| OZID_52 | F0209 | 22134 | 25208 | phage morphogenesis protein |
| OZID_52 | F0210 | 25208 | 25537 | phage morphogenesis protein |
| OZID_52 | F0211 | 25547 | 26245 | phage morphogenesis protein |
| OZID_52 | F0212 | 26251 | 26994 | phage morphogenesis protein |
| OZID_52 | F0213 | 26892 | 27539 | phage morphogenesis protein |
| OZID_52 | F0214 | 27600 | 28307 | phage morphogenesis protein |
| OZID_52 | F0215 | 28222 | 31017 | phage morphogenesis protein |
| OZID_52 | F0216 | 31088 | 31687 | |
| OZID_52 | F0217 | 31747 | 33063 | phage tail protein |
| OZID_52 | F0218 | 33511 | 34491 | |
| OZID_52 | F0220 | 34525 | 35544 | |
| OZID_52 | F0221 | 36646 | 37254 | |
| OZID_52 | F0222 | 37485 | 38183 | |
| OZID_53 | F0223 | 607 | 2619 | |
| OZID_53 | F0225 | 2546 | 2749 | |
| OZID_55 | F0231 | 400 | 71 | |
| OZID_55 | F0232 | 776 | 390 | |
| OZID_56 | F0233 | 287 | 1630 | |
| OZID_56 | F0234 | 1652 | 1972 | |
| OZID_56 | F0235 | 1984 | 3465 | putative sulfatase |
| OZID_57 | F0236 | 606 | 1847 | |
| OZID_57 | F0237 | 1957 | 2412 | |
| OZID_59 | F0239 | 161 | 1363 | putative P4-family integrase |
| OZID_59 | F0240 | 3367 | 1550 | |
| OZID_59 | F1480 | 3564 | 3659 | transposase |
| OZID_59 | F1481 | 3660 | 3836 | transposase |
| OZID_59 | F0242 | 3855 | 4025 | |
| OZID_59 | F0243 | 3863 | 4300 | transposase |
| OZID_59 | F0241 | 4159 | 3821 | |
| OZID_59 | F0244 | 4467 | 4775 | putative prophage regulatory protein |
| OZID_59 | F0245 | 5400 | 6803 | |
| OZID_59 | F0246 | 7624 | 8187 | |
| OZID_59 | F0247 | 8318 | 10702 | |
| OZID_59 | F0248 | 12997 | 11459 | unknown in ISEc8 |
| OZID_59 | F0249 | 13394 | 13047 | unknown in ISEc8 |
| OZID_59 | F0250 | 13792 | 13391 | unknown in ISEc8 |
| OZID_59 | F0251 | 14158 | 13847 | putative transposase |
| OZID_59 | F0252 | 14298 | 15116 | unknown in IS600 |
| OZID_59 | F0253 | 15229 | 15768 | putative complement resistance protein |
| OZID_59 | F0254 | 17067 | 17426 | putative diacylglycerol kinase |
| OZID_59 | F0255 | 19138 | 17519 | |

TABLE 2-continued

| Sequence_ID | Orf_ID | Orf_Start | Orf_End | Description |
| --- | --- | --- | --- | --- |
| OZID_59 | F0256 | 20019 | 20717 | putative urease accessory protein D |
| OZID_59 | F0257 | 20808 | 21110 | putative urease structural subunit A (gamma) |
| OZID_59 | F0258 | 21119 | 21439 | putative urease structural subunit B (beta) |
| OZID_59 | F0259 | 21414 | 23135 | putative urease structural subunit C (alpha) |
| OZID_59 | F0260 | 23145 | 23609 | putative urease accessory protein E |
| OZID_59 | F0261 | 23610 | 24284 | putative urease accessory protein |
| OZID_59 | F0262 | 24296 | 24913 | putative urease accessory protein |
| OZID_59 | F0263 | 24900 | 24514 | |
| 0710_59 | F0264 | 25510 | 25169 | unknown in IS |
| OZID_59 | F0265 | 26125 | 26388 | putative ribosomal protein |
| OZID_59 | F0266 | 27139 | 26762 | |
| OZID_59 | F0267 | 27657 | 27262 | putative colicin immunity protein |
| OZID_59 | F0268 | 28440 | 27703 | |
| OZID_59 | F0269 | 29449 | 30210 | |
| OZID_59 | F0271 | 30391 | 30660 | |
| OZID_59 | F0270 | 30524 | 29907 | unknown in ISEc8 |
| OZID_59 | F0272 | 30712 | 31137 | unknown in ISEc8 |
| OZID_59 | F0273 | 31134 | 31484 | unknown in ISEc8 |
| OZID_59 | F0274 | 31515 | 33128 | unknown in ISEc8 |
| OZID_59 | F0276 | 33378 | 33674 | |
| OZID_59 | F0277 | 33747 | 34490 | |
| OZID_59 | F0275 | 33989 | 33132 | unknown in ISEc8 |
| OZID_59 | F0278 | 34412 | 34071 | unknown in ISEc8 |
| OZID_59 | F0279 | 34728 | 34399 | unknown in ISEc8 |
| OZID_59 | F0280 | 35456 | 34989 | unknown associated with putative tellurite resistance |
| OZID_59 | F0281 | 36682 | 35474 | |
| OZID_59 | F0282 | 37649 | 36693 | |
| OZID_59 | F0283 | 38728 | 37649 | |
| OZID_59 | F0284 | 39503 | 38730 | |
| OZID_59 | F0285 | 40638 | 39496 | |
| OZID_59 | F0286 | 41706 | 40648 | |
| OZID_59 | F0287 | 42029 | 42610 | putative phage inhibition, colicin resistance and tellurite resistance protein |
| OZID_59 | F0288 | 42610 | 43767 | putative phage inhibition, colicin resistance and tellurite resistance protein |
| OZID_59 | F0289 | 43790 | 44245 | putative phage inhibition, colicin resistance and tellurite resistance protein |
| OZID_59 | F0290 | 44268 | 45308 | putative phage inhibition, colicin resistance and tellurite resistance protein |
| OZID_59 | F0292 | 45357 | 45935 | putative phage inhibition, colicin resistance and tellurite resistance protein |
| OZID_59 | F0293 | 46004 | 46579 | putative phage inhibition, colicin resistance and tellurite resistance protein |
| OZID_59 | F0294 | 49991 | 47901 | putative receptor |
| OZID_59 | F0295 | 51424 | 51663 | |
| OZID_59 | F0296 | 52296 | 52631 | |
| OZID_59 | F0297 | 52742 | 52933 | |
| OZID_59 | F0299 | 53542 | 53910 | |
| OZID_59 | F0298 | 53606 | 53412 | |
| OZID_59 | F0300 | 53837 | 53658 | |
| OZID_59 | F0301 | 53926 | 54198 | |
| OZID_59 | F0302 | 54131 | 53934 | |
| OZID_59 | F0303 | 54482 | 54697 | |
| OZID_59 | F0305 | 54763 | 54960 | |
| OZID_59 | F0304 | 54824 | 54603 | |
| OZID_59 | F0306 | 55202 | 54867 | |
| OZID_59 | F0307 | 55690 | 56814 | putative glucosyltransferase |
| OZID_59 | F1483 | 57658 | 57233 | transposase |
| OZID_59 | F1484 | 57930 | 57655 | transposase |
| OZID_59 | F0308 | 59084 | 59593 | |

TABLE 2-continued

| Sequence_ID | Orf_ID | Orf_Start | Orf_End | Description |
|---|---|---|---|---|
| OZID_59 | F0309 | 59682 | 60305 | |
| OZID_59 | F0311 | 60401 | 60634 | |
| OZID_59 | F0312 | 61243 | 61497 | |
| OZID_59 | F0313 | 62359 | 61472 | putative transposase |
| OZID_59 | F0314 | 62685 | 62359 | unknown in IS |
| OZID_59 | F0315 | 62866 | 63912 | |
| OZID_59 | F0316 | 64153 | 64668 | |
| OZID_59 | F0317 | 64818 | 66833 | |
| OZID_59 | F0318 | 67334 | 68566 | |
| OZID_59 | F0319 | 68551 | 69189 | |
| OZID_59 | F0320 | 69558 | 70202 | |
| OZID_59 | F0321 | 70518 | 71018 | |
| OZID_59 | F1485 | 71151 | 70900 | transposase |
| OZID_59 | F0323 | 71202 | 71627 | unknown in putative ISEc8 |
| OZID_59 | F0324 | 72399 | 73310 | |
| OZID_59 | F0325 | 73514 | 76531 | putative adhesin |
| OZID_59 | F0326 | 76639 | 79026 | |
| OZID_59 | F0327 | 79023 | 79928 | |
| OZID_59 | F0328 | 79925 | 80995 | |
| OZID_59 | F0329 | 81335 | 82153 | |
| OZID_59 | F0330 | 82244 | 82729 | |
| OZID_59 | F0331 | 82730 | 83221 | putative DNA repair protein |
| OZID_59 | F0332 | 83284 | 83505 | |
| OZID_59 | F0333 | 83668 | 84042 | putative structural protein |
| OZID_59 | F0334 | 84089 | 84370 | |
| OZID_59 | F0335 | 85232 | 84345 | putative transposase |
| OZID_59 | F0336 | 85558 | 85232 | unknown in IS |
| OZID_59 | F0339 | 86558 | 87400 | |
| OZID_59 | F0340 | 87457 | 86912 | |
| OZID_62 | F0342 | 1161 | 142 | integrase |
| OZID_62 | F0343 | 1381 | 1139 | |
| OZID_62 | F0344 | 3920 | 1449 | |
| OZID_62 | F0345 | 4142 | 4014 | |
| OZID_62 | F0346 | 4390 | 4202 | cell division inhibition protein |
| OZID_62 | F0347 | 5726 | 5337 | |
| OZID_62 | F0348 | 5866 | 5738 | |
| OZID_62 | F0349 | 6023 | 5868 | |
| OZID_62 | F0350 | 6779 | 6588 | |
| OZID_62 | F0351 | 7208 | 6807 | |
| OZID_62 | F0352 | 7573 | 7998 | |
| OZID_62 | F0353 | 7961 | 8521 | |
| OZID_62 | F0354 | 8582 | 8205 | |
| OZID_62 | F0355 | 8628 | 9830 | |
| OZID_62 | F0356 | 8855 | 8700 | |
| OZID_62 | F0357 | 9837 | 10583 | DNA replication factor |
| OZID_62 | F0358 | 10605 | 11375 | |
| OZID_62 | F0359 | 11391 | 11804 | |
| OZID_62 | F0360 | 12929 | 12156 | |
| OZID_62 | F0362 | 13888 | 14061 | |
| OZID_62 | F0363 | 14137 | 15186 | |
| OZID_62 | F0364 | 15199 | 15570 | endodeoxyribonuclease |
| OZID_62 | F0365 | 15551 | 15931 | |
| OZID_62 | F0366 | 16077 | 16901 | |
| OZID_62 | F0367 | 17188 | 17427 | |
| OZID_62 | F0368 | 17522 | 18235 | regulatory protein |
| OZID_62 | F0369 | 19003 | 20853 | |
| OZID_62 | F0370 | 21029 | 21355 | unknown in IS |
| OZID_62 | F0371 | 21352 | 22005 | transposase |
| OZID_62 | F0372 | 22524 | 22210 | regulatory protein |
| OZID_62 | F0373 | 23457 | 22990 | cell lysis protein |
| OZID_62 | F0374 | 24274 | 23777 | cell lysis protein |
| OZID_62 | F0375 | 24326 | 24144 | cell lysis protein |
| OZID_62 | F0377 | 24444 | 24758 | |
| OZID_62 | F0376 | 24553 | 24359 | |
| OZID_62 | F0378 | 25220 | 25014 | cell lysis protein |
| OZID_62 | F1393 | 27518 | 25668 | |
| OZID_62 | F1394 | 28000 | 27833 | |
| OZID_62 | F1440 | 28127 | 27840 | |
| OZID_62 | F1396 | 29436 | 29065 | |
| OZID_62 | F1397 | 29759 | 29376 | |
| OZID_62 | F1398 | 30109 | 29750 | |
| OZID_62 | F1399 | 31225 | 30122 | |
| OZID_62 | F1400 | 31445 | 31173 | |
| OZID_62 | F1401 | 31779 | 31567 | |
| OZID_62 | F1403 | 32229 | 32459 | |

TABLE 2-continued

| Sequence_ID | Orf_ID | Orf_Start | Orf_End | Description |
|---|---|---|---|---|
| OZID_62 | F1402 | 32241 | 32029 | |
| OZID_62 | F1404 | 33032 | 32475 | |
| OZID_62 | F1405 | 33660 | 33355 | |
| OZID_62 | F1406 | 33691 | 33380 | |
| OZID_62 | F1407 | 34313 | 33909 | |
| OZID_62 | F1408 | 34939 | 34223 | |
| OZID_62 | F1409 | 35635 | 34973 | |
| OZID_62 | F1410 | 36476 | 35427 | |
| OZID_62 | F1411 | 37036 | 36539 | |
| OZID_62 | F1412 | 37282 | 37920 | |
| OZID_62 | F1413 | 38132 | 38365 | |
| OZID_62 | F1414 | 38365 | 39015 | |
| OZID_62 | F1415 | 39688 | 39981 | |
| OZID_62 | F1416 | 40259 | 41503 | |
| OZID_62 | F1417 | 41500 | 42036 | putative transposase |
| OZID_62 | F1418 | 42109 | 42456 | |
| OZID_62 | F1491 | 42883 | 43007 | heat stable enterotoxin |
| OZID_62 | F1419 | 43387 | 42506 | putative transposase |
| OZID_62 | F1420 | 43398 | 43799 | unknown in ISEc8 |
| OZID_62 | F1048B | 43796 | 44143 | unknown in ISEc8 |
| OZID_62 | F1388 | 46165 | 45743 | putative transposase |
| OZID_62 | F1387 | 46965 | 46315 | |
| OZID_62 | F1386 | 47297 | 46950 | |
| OZID_62 | F1385 | 48206 | 47676 | |
| OZID_62 | F1384A | 48540 | 48866 | unknown in IS |
| OZID_62 | F1383 | 48863 | 49753 | putative IS629 transposase |
| OZID_63 | F1472 | 212 | 613 | |
| OZID_63 | F1473 | 1491 | 739 | |
| OZID_64 | L0061 | 1363 | 29 | integrase |
| OZID_64 | L0062 | 1691 | 1392 | putative excisionase |
| OZID_64 | L0063 | 2073 | 1762 | |
| OZID_64 | L0064 | 2498 | 2133 | |
| OZID_64 | L0065 | 3033 | 2410 | |
| OZID_64 | L0066 | 3324 | 3037 | |
| OZID_64 | L0067 | 3544 | 3326 | |
| OZID_64 | L0068 | 3833 | 3546 | |
| OZID_64 | L0069 | 4876 | 4103 | |
| OZID_64 | L0070 | 5474 | 5193 | |
| OZID_64 | L0071 | 5676 | 5485 | |
| OZID_64 | L0072 | 5837 | 5649 | |
| OZID_64 | L0073 | 6508 | 5831 | exonuclease |
| OZID_64 | L0074 | 7290 | 6505 | recombination protein |
| OZID_64 | L0075 | 7592 | 7296 | host-nuclease inhibitor protein |
| OZID_64 | L0076 | 7937 | 7668 | kil protein |
| OZID_64 | L0077 | 7944 | 7780 | regulatory protein CIII |
| OZID_64 | L0078 | 8385 | 8017 | putative single-stranded DNA binding protein |
| OZID_64 | L0079 | 9006 | 8536 | |
| OZID_64 | L0080 | 9448 | 9065 | early gene regulator N |
| OZID_64 | L0081 | 10101 | 9937 | |
| OZID_64 | L0082 | 11150 | 10104 | serine/threonine kinase |
| OZID_64 | L0083 | 11605 | 11144 | |
| OZID_64 | L0084 | 12014 | 11673 | |
| OZID_64 | L0085 | 12782 | 12075 | repressor protein CI |
| OZID_64 | L0086 | 12861 | 13088 | regulatory protein Cro |
| OZID_64 | L0087 | 13227 | 13523 | regulatory protein CII |
| OZID_64 | L0088 | 13556 | 14494 | replication protein O |
| OZID_64 | L0089 | 14491 | 15192 | replication protein P |
| OZID_64 | L0090 | 15189 | 15479 | Ren protein |
| OZID_64 | L0091 | 15550 | 15828 | |
| OZID_64 | L0092 | 15997 | 16356 | |
| OZID_64 | L0093 | 16380 | 16826 | |
| OZID_64 | L0094 | 16823 | 17350 | putative DNA N-6-adenine-methyltransferase |
| OZID_64 | L0095 | 17532 | 18581 | |
| OZID_64 | L0096 | 18727 | 19455 | DNA-binding protein Roi |
| OZID_64 | L0097 | 19455 | 20060 | |
| OZID_64 | L0098 | 20057 | 20251 | |
| OZID_64 | L0099 | 20205 | 20678 | late gene regulator Q |
| OZID_64 | L0103 | 21462 | 22421 | Shiga toxin 2 subunit A |
| OZID_64 | L0104 | 22433 | 22702 | Shiga toxin 2 subunit B |
| OZID_64 | L0105 | 23189 | 25126 | |
| OZID_64 | L0106 | 25307 | 25753 | |
| OZID_64 | L0107 | 25830 | 26045 | lysis protein S; holin |
| OZID_64 | L0108 | 26050 | 26583 | endolysin |
| OZID_64 | L0109 | 26854 | 27423 | putative regulatory protein |

TABLE 2-continued

| Sequence_ID | Orf_ID | Orf_Start | Orf_End | Description |
|---|---|---|---|---|
| OZID_64 | L0110 | 27577 | 28041 | endopeptidase |
| OZID_64 | L0143 | 27797 | 27982 | Rz1 protein precursor; prolipoprotein; outer membrane lipoprote |
| OZID_64 | L0111 | 28366 | 28073 | Bor protein precursor |
| OZID_64 | L0112 | 28775 | 29581 | putative terminase, small subunit |
| OZID_64 | L0113 | 29562 | 31268 | putative terminase, large subunit |
| OZID_64 | L0114 | 31268 | 33412 | putative portal protein |
| OZID_64 | L0115 | 33570 | 34577 | |
| OZID_64 | L0116 | 34601 | 35815 | |
| OZID_64 | L0117 | 35871 | 36260 | |
| OZID_64 | L0118 | 36283 | 36771 | |
| OZID_64 | L0119 | 36647 | 37318 | |
| OZID_64 | L0120 | 37318 | 37968 | |
| OZID_64 | L0121 | 37965 | 39902 | putative tail fiber protein |
| OZID_64 | L0122 | 39784 | 40173 | |
| OZID_64 | L0123 | 40220 | 40501 | |
| OZID_64 | L0124 | 40718 | 42421 | |
| OZID_64 | L0125 | 42418 | 43686 | |
| OZID_64 | L0126 | 43752 | 43979 | |
| OZID_64 | L0127 | 43985 | 44602 | |
| OZID_64 | L0128 | 44693 | 45427 | outer membrane protein Lom precursor |
| OZID_64 | L0129 | 45857 | 46258 | |
| OZID_64 | L0130 | 46352 | 47008 | |
| OZID_64 | L0131 | 47011 | 47457 | |
| OZID_64 | L0132 | 47467 | 47718 | |
| OZID_64 | L0133 | 47729 | 48994 | |
| OZID_64 | L0134 | 49025 | 57445 | |
| OZID_64 | L0135 | 57728 | 57916 | |
| OZID_64 | L0136 | 58340 | 57996 | |
| OZID_64 | L0137 | 58615 | 58460 | host killer protein |
| OZID_64 | L0144 | 58672 | 58460 | modulation of host killing; part of toxin/antitoxin system; prophage maintenance |
| OZID_64 | L0139 | 59376 | 58906 | |
| OZID_64 | L0141 | 60418 | 60197 | |
| OZID_64 | L0142 | 61095 | 60466 | |
| OZID_65 | F0379 | 1491 | 148 | |
| OZID_66 | F0380 | 87 | 1697 | |
| OZID_66 | F0381 | 2291 | 1764 | |
| OZID_66 | F0382 | 2692 | 2853 | |
| OZID_66 | F0383 | 3787 | 4578 | putative oxidoreductase |
| OZID_66 | F0384 | 5368 | 4724 | putative chaperone |
| OZID_66 | F0385 | 6744 | 5410 | |
| OZID_66 | F0386 | 9282 | 6760 | putative usher protein |
| OZID_66 | F0387 | 10057 | 9335 | putative chaperone |
| OZID_66 | F0389 | 10682 | 10122 | putative pilin subunit |
| OZID_66 | F0390 | 11348 | 10725 | |
| OZID_66 | F0391 | 12739 | 16551 | putative member of ShlA/HecA/FhaA exoprotein family |
| OZID_66 | F0393 | 16640 | 18259 | putative outer membrane transporter of ShlA/HecA/FhaA exoprotein family |
| OZID_66 | F0394 | 18275 | 18643 | putative acyl-carrier protein synthase |
| OZID_66 | F0395 | 18654 | 19418 | putative fatty acyl chain reductase |
| OZID_66 | F0396 | 19422 | 19970 | putative fatty acyl chain dehydrase |
| OZID_66 | F0397 | 19992 | 20273 | putative acyl-carrier protein |
| OZID_66 | F0398 | 20309 | 21469 | putative aminomethyltransferase |
| OZID_66 | F0399 | 21543 | 24101 | putative beta-ketoacyl-acyl carrier protein synthase |
| OZID_66 | F0401 | 24040 | 25329 | |
| OZID_66 | F0402 | 25326 | 26279 | |
| OZID_66 | F0403 | 26203 | 26997 | |
| OZID_66 | F0404 | 26990 | 27637 | |
| OZID_66 | F0405 | 27638 | 28948 | |
| OZID_66 | F0406 | 28957 | 29745 | |
| OZID_66 | F0407 | 29742 | 31130 | |
| OZID_68 | F1338 | 5046 | 6371 | |
| OZID_68 | F0634 | 8543 | 8271 | |
| OZID_69 | F0410 | 102 | 344 | |

TABLE 2-continued

| Sequence_ID | Orf_ID | Orf_Start | Orf_End | Description |
| --- | --- | --- | --- | --- |
| OZID_69 | F0411 | 429 | 1271 | |
| OZID_7 | F0013 | 3203 | 2094 | putative fimbrial protein |
| OZID_7 | F0014 | 3805 | 3215 | putative fimbrial protein |
| OZID_7 | F0015 | 4431 | 3826 | putative fimbrial protein |
| OZID_7 | F0016 | 5006 | 4446 | putative fimbrial protein |
| OZID_7 | F0017 | 7506 | 5008 | putative fimbrial usher protein |
| OZID_7 | F0018 | 8381 | 7650 | putative fimbrial chaperone protein |
| OZID_7 | F0019 | 9067 | 8462 | putative fimbrial protein |
| OZID_71 | F0412 | 375 | 145 | integrase |
| OZID_71 | F0413 | 1063 | 476 | integrase |
| OZID_71 | F0414 | 1510 | 1232 | excisionase |
| OZID_71 | F0416 | 1968 | 2381 | |
| OZID_71 | F0415 | 2000 | 1563 | |
| OZID_71 | F0417 | 2488 | 2261 | |
| OZID_71 | F0419 | 3658 | 3182 | |
| OZID_71 | F0420 | 4090 | 4515 | |
| OZID_71 | F0421 | 4578 | 5621 | |
| OZID_71 | F0422 | 5413 | 6075 | |
| OZID_71 | F0423 | 6109 | 6825 | |
| OZID_71 | F0424 | 6735 | 7139 | |
| OZID_71 | F0425 | 7136 | 7438 | |
| OZID_71 | F0426 | 7428 | 7745 | |
| OZID_71 | F0427 | 7687 | 8016 | |
| OZID_71 | F0428 | 8003 | 8440 | |
| OZID_71 | F0429 | 8636 | 9223 | |
| OZID_71 | F0430 | 10292 | 11341 | |
| OZID_71 | F0431 | 11354 | 11728 | endonuclease |
| OZID_71 | F0432 | 11725 | 12546 | phage late gene regulator Q |
| OZID_71 | F0433 | 13143 | 13310 | |
| OZID_71 | F0434 | 13625 | 15562 | |
| OZID_71 | F0435 | 15710 | 15892 | |
| OZID_71 | F0436 | 15819 | 16199 | |
| OZID_71 | F0437 | 16275 | 16490 | |
| OZID_71 | F0952 | 16890 | 17423 | cell lysis protein |
| OZID_71 | F0951 | 17694 | 18263 | antirepressor |
| OZID_71 | F1348 | 19516 | 19881 | |
| OZID_71 | F1349 | 19598 | 19987 | |
| OZID_71 | F1350 | 20171 | 20734 | |
| OZID_71 | F0945 | 20731 | 22392 | |
| OZID_71 | F1352 | 22456 | 24393 | |
| OZID_71 | F1353 | 24438 | 24659 | |
| OZID_72 | F0439 | 234 | 1 | unknown in IS |
| OZID_72 | F0441 | 514 | 867 | putative transposase |
| OZID_72 | F0440 | 602 | 396 | unknown in IS |
| OZID_72 | F0442 | 1009 | 1242 | |
| OZID_72 | F0443 | 1370 | 1095 | |
| OZID_72 | F0444 | 2792 | 1431 | |
| OZID_73 | F0447 | 146 | 1396 | integrase |
| OZID_73 | F0448 | 1761 | 1949 | |
| OZID_73 | F0449 | 2007 | 2750 | |
| OZID_73 | F0450 | 2776 | 2973 | |
| OZID_73 | F0451 | 2924 | 3151 | |
| OZID_73 | F0452 | 3151 | 3342 | |
| OZID_73 | F0453 | 3332 | 3574 | |
| OZID_73 | F0454 | 3580 | 3879 | |
| OZID_73 | F0455 | 3876 | 6008 | |
| OZID_73 | F0456 | 6379 | 6630 | |
| OZID_73 | F0457 | 6627 | 7037 | ssDNA-binding protein |
| OZID_73 | F0458 | 7006 | 7320 | |
| OZID_73 | F0459 | 7367 | 7669 | |
| OZID_73 | F0460 | 7962 | 9119 | |
| OZID_73 | F0461 | 9159 | 9731 | |
| OZID_73 | F0462 | 9733 | 10944 | |
| OZID_73 | F0463 | 10941 | 11279 | |
| OZID_73 | F0464 | 11276 | 11572 | |
| OZID_73 | F0465 | 11572 | 12012 | |
| OZID_73 | F0466 | 12302 | 12658 | |
| OZID_73 | F0467 | 12774 | 14066 | |
| OZID_73 | F0468 | 13894 | 14304 | |
| OZID_73 | F0469 | 14318 | 14599 | |
| OZID_74 | F0470 | 1203 | 61 | integrase |
| OZID_74 | F0471 | 1429 | 1193 | excisionase |
| OZID_74 | F0472 | 1460 | 1618 | |
| OZID_74 | F0473 | 1533 | 2135 | phage replication protein |
| OZID_74 | F0474 | 2135 | 2356 | phage replication protein |

TABLE 2-continued

| Sequence_ID | Orf_ID | Orf_Start | Orf_End | Description |
|---|---|---|---|---|
| OZID_74 | F0475 | 2353 | 3054 | phage replication protein |
| OZID_74 | F0476 | 3051 | 3353 | |
| OZID_74 | F0477 | 3421 | 3753 | |
| OZID_74 | F0478 | 3998 | 5524 | |
| OZID_74 | F0479 | 5644 | 5835 | |
| OZID_74 | F0480 | 6026 | 6481 | |
| OZID_74 | F0481 | 6481 | 6651 | |
| OZID_74 | F0482 | 6644 | 6934 | |
| OZID_74 | F0483 | 6931 | 7293 | endonuclease |
| OZID_74 | F0484 | 7427 | 8116 | phage late gene regulator Q |
| OZID_74 | F0485 | 8438 | 8743 | |
| OZID_74 | F0486 | 8730 | 9206 | cell lysis protein |
| OZID_74 | F0487 | 9203 | 9664 | cell lysis protein |
| OZID_74 | F0488 | 9989 | 9696 | membrane protein |
| OZID_74 | F0489 | 10733 | 10281 | |
| OZID_74 | F0490 | 10977 | 11183 | |
| OZID_74 | F0491 | 11542 | 11348 | |
| OZID_74 | F0492 | 11931 | 12476 | phage DNA packaging protein |
| OZID_74 | F0493 | 12451 | 14376 | phage DNA packaging protein |
| OZID_74 | F0494 | 14373 | 14579 | phage morphogenesis protein |
| OZID_74 | F0495 | 14576 | 16177 | phage capsid protein |
| OZID_74 | F0496 | 16023 | 16394 | phage capsid protein |
| OZID_74 | F0497 | 16391 | 17476 | phage capsid protein |
| OZID_74 | F0498 | 17480 | 17818 | phage morphogenesis protein |
| OZID_74 | F0499 | 17847 | 18899 | phage capsid protein |
| OZID_74 | F0500 | 18902 | 19339 | phage DNA packaging protein |
| OZID_74 | F0501 | 19351 | 19704 | phage morphogenesis protein |
| OZID_74 | F0502 | 19719 | 20252 | phage tail protein |
| OZID_74 | F0503 | 20249 | 20644 | phage tail protein |
| OZID_74 | F0504 | 20652 | 21404 | phage tail protein |
| OZID_74 | F0505 | 21418 | 21840 | phage tail protein |
| OZID_74 | F0506 | 21867 | 22226 | phage tail protein |
| OZID_74 | F0508 | 22263 | 24875 | phage tail protein |
| OZID_74 | F0509 | 24872 | 25201 | phage tail protein |
| OZID_74 | F0510 | 25201 | 25899 | phage tail protein |
| OZID_74 | F1426 | 25739 | 26653 | phage tail protein |
| OZID_74 | F0512 | 26551 | 27228 | phage tail protein |
| OZID_74 | F0513 | 27469 | 28644 | phage tail protein |
| OZID_74 | F0514 | 28521 | 30941 | phage tail protein |
| OZID_74 | F0515 | 31009 | 31608 | membrane protein |
| OZID_74 | F0820 | 31667 | 34588 | putative tail fiber protein |
| OZID_74 | F0821 | 32919 | 32170 | |
| OZID_74 | F0819 | 34588 | 35169 | putative tail fiber protein |
| OZID_74 | F0818 | 36179 | 35289 | |
| OZID_74 | F0817 | 36704 | 36198 | |
| OZID_74 | F0816 | 37247 | 36741 | |
| OZID_74 | F0815 | 37502 | 37320 | |
| OZID_74 | F0814 | 38668 | 38000 | |
| OZID_74 | F0813 | 38725 | 38973 | |
| OZID_74 | F0811 | 39426 | 39773 | |
| OZID_74 | F0771 | 39823 | 41361 | |
| OZID_74 | F0808 | 43148 | 41664 | possible protease (ompP-like) |
| OZID_74 | F0807 | 44288 | 43335 | putative OmpT-like protease |
| OZID_74 | F0806 | 44770 | 45105 | |
| OZID_77 | F0522 | 933 | 43 | transposase |
| OZID_77 | F0523 | 1256 | 930 | unknown in IS |
| OZID_78 | F0525 | 2827 | 1973 | putative molybdenum transport protein |
| OZID_78 | F0526 | 3636 | 2992 | |
| OZID_78 | F0527 | 4404 | 3646 | putative iron compound ABC transporter, ATP-binding protein |
| OZID_78 | F0528 | 5381 | 4401 | putative iron compound ABC transporter, permease protein |
| OZID_78 | F0529 | 6403 | 5381 | |
| OZID_81 | F0530 | 1174 | 44 | integrase |
| OZID_81 | F0531 | 3936 | 1465 | |
| OZID_81 | F0533 | 6911 | 7066 | |
| OZID_81 | F0534 | 7593 | 8480 | |
| OZID_81 | F0535 | 8420 | 9085 | |
| OZID_81 | F0536 | 9272 | 9853 | |
| OZID_81 | F0537 | 10713 | 11471 | |
| OZID_81 | F0538 | 12790 | 13836 | |
| OZID_81 | F0539 | 13849 | 14208 | endonuclease |
| OZID_81 | F0540 | 14217 | 14747 | |
| OZID_81 | F0541 | 14866 | 15186 | |

TABLE 2-continued

| Sequence_ID | Orf_ID | Orf_Start | Orf_End | Description |
| --- | --- | --- | --- | --- |
| OZID_81 | F0542 | 15337 | 16395 | |
| OZID_81 | F0543 | 17296 | 19041 | |
| OZID_81 | F0544 | 19490 | 19696 | |
| OZID_81 | F0545 | 19698 | 20045 | |
| OZID_81 | F0546 | 20096 | 20629 | cell lysis protein |
| OZID_81 | F0547 | 20903 | 21598 | antirepressor |
| OZID_81 | F0548 | 21821 | 22294 | cell lysis protein |
| OZID_81 | F0550 | 22618 | 22959 | membrane protein |
| OZID_81 | F0551 | 23333 | 23698 | |
| OZID_81 | F0552 | 23987 | 24550 | phage DNA packaging protein |
| OZID_81 | F0553 | 24528 | 26207 | |
| OZID_81 | F0555 | 26271 | 27884 | |
| OZID_81 | F0556 | 28419 | 30998 | |
| OZID_81 | F0557 | 31001 | 31327 | |
| OZID_81 | F0558 | 31337 | 31687 | |
| OZID_81 | F0559 | 31684 | 32130 | |
| OZID_81 | F0560 | 32127 | 32471 | |
| OZID_81 | F0561 | 32468 | 33271 | |
| OZID_81 | F0565 | 33996 | 37076 | phage tail protein |
| OZID_81 | F0566 | 37111 | 37410 | phage tail protein |
| OZID_81 | F0567 | 37410 | 37847 | phage tail protein |
| OZID_84 | F0661 | 1059 | 1454 | |
| OZID_87 | F0659 | 179 | 742 | putative type 1 pilin protein |
| OZID_87 | F0658 | 1014 | 1814 | putative fimbrial protein chaperone |
| OZID_88 | F0655 | 823 | 602 | |
| OZID_88 | F0654 | 983 | 1492 | |
| OZID_91 | F0651 | 574 | 365 | |
| OZID_91 | F0650 | 795 | 574 | |
| OZID_92 | F0646 | 4422 | 2278 | |
| OZID_93 | F0645 | 420 | 43 | |
| OZID_93 | F0644 | 976 | 545 | |
| OZID_93 | F0643 | 1331 | 963 | |
| OZID_93 | F0642 | 1731 | 1306 | |
| OZID_95 | F0640 | 3892 | 818 | |
| OZID_96 | F0639 | 836 | 195 | |
| OZID_96 | F0638 | 1547 | 918 | |
| OZID_96 | F0637 | 2195 | 1620 | |
| OZID_96 | F0636 | 2577 | 2308 | |
| OZID_96 | F0635 | 3148 | 2579 | |
| OZID_98 | F0631 | 3745 | 272 | phage tail protein |
| OZID_98 | F0630 | 3879 | 4406 | superoxide dismutase |
| OZID_98 | F0629 | 5274 | 4597 | phage tail protein |
| OZID_98 | F0628 | 6086 | 5172 | phage tail protein |
| OZID_98 | F0627 | 6624 | 5926 | phage tail protein |
| OZID_98 | F0626 | 6953 | 6624 | phage tail protein |
| OZID_98 | F0625 | 7714 | 6950 | phage tail protein |
| OZID_98 | F0624 | 9528 | 7666 | phage tail protein |
| OZID_98 | F0623 | 9922 | 9509 | phage tail protein |
| OZID_98 | F0622 | 10452 | 9949 | phage tail protein |
| OZID_98 | F0621 | 11023 | 10394 | phage tail protein |
| OZID_98 | F0620 | 11382 | 11116 | phage capsid protein |
| OZID_98 | F0619 | 11787 | 11440 | phage capsid protein |
| OZID_98 | F0618 | 13329 | 11824 | phage morphogenesis protein |
| OZID_98 | F0617 | 14911 | 13319 | phage morphogenesis protein |
| OZID_98 | F0616 | 15114 | 14908 | phage morphogenesis protein |
| OZID_98 | F0615 | 17062 | 15098 | phage DNA packaging protein |
| OZID_98 | F0614 | 17507 | 16998 | |
| OZID_98 | F0613 | 17902 | 18126 | |
| OZID_98 | F0612 | 18522 | 18208 | |
| OZID_98 | F0611 | 18904 | 18764 | |
| OZID_98 | F0610 | 19454 | 18987 | cell lysis protein |
| OZID_98 | F0609 | 19866 | 19606 | |
| OZID_98 | F0608 | 20095 | 19859 | |
| OZID_98 | F0607 | 20477 | 19944 | cell lysis protein |
| OZID_98 | F0606 | 20872 | 20564 | |
| OZID_98 | F0605 | 21083 | 20877 | cell lysis protein |
| OZID_98 | F1486 | 21403 | 21729 | transposase |
| OZID_98 | F0604 | 21726 | 22616 | transposase |
| OZID_98 | F0603 | 22582 | 22917 | |
| OZID_98 | F0602 | 24548 | 22698 | |
| OZID_98 | F0601 | 25126 | 24959 | |
| OZID_98 | F0600 | 25253 | 24966 | |
| OZID_98 | F0599 | 25626 | 25123 | |
| OZID_98 | F0598 | 25843 | 25505 | |
| OZID_98 | F1373 | 26030 | 26296 | |

TABLE 2-continued

| Sequence_ID | Orf_ID | Orf_Start | Orf_End | Description |
|---|---|---|---|---|
| OZID_98 | F0597 | 26790 | 26116 | |
| OZID_98 | F0596 | 26957 | 26667 | |
| OZID_98 | F0595 | 27555 | 27046 | |
| OZID_98 | F0594 | 27709 | 27458 | |
| OZID_98 | F0593 | 28055 | 28963 | |
| OZID_98 | F0592 | 29077 | 29445 | |
| OZID_98 | F0591 | 29442 | 30434 | |
| OZID_98 | F0590 | 31553 | 30402 | cytosine methylase |
| OZID_98 | F0589 | 32242 | 31985 | |
| OZID_98 | F0588 | 32403 | 32242 | |
| OZID_98 | F0587 | 32470 | 32309 | |
| OZID_98 | F0586 | 32744 | 32481 | |
| OZID_98 | F0585 | 33208 | 32996 | |
| OZID_98 | F0584 | 33736 | 33314 | |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6855814B2). An electronic copy of the "Sequence Listing" will also be available from the USPTO upon request and payment of the fee set forth in 37 CFR 1.19(b)(3).

We claim:

1. An isolated DNA molecule comprising the nucleotide sequence of SEQ ID NO:256.

2. A recombinant DNA construction comprising the isolated DNA molecule of claim 1.

3. A method for detecting *Escherichia coli* O157:H7 (ATCC 43895) in a sample comprising the steps of:
   a) providing an *E. coli* O157:H7-specific nucleotide probe, the probe comprising a sequence as set forth in SEQ ID NO:256;
   b) contacting the probe with a sample of test material under suitable hybridization conditions; and
   c) detecting hybridization of the probe to a complementary nucleotide sequence in the sample.

4. A method for distinguishing *E. coli* bacteria of strain O157:H7 from strain K12 comprising analyzing the genome of the bacteria for the presence of a sequence comprising SEQ ID NO: 256 by the method of claim 3.

* * * * *